(12) United States Patent
Decrulle et al.

(10) Patent No.: US 11,839,645 B2
(45) Date of Patent: Dec. 12, 2023

(54) THERAPEUTIC USE OF ENGINEERED POSTBIOTICS COMPRISING BACTERIOCINS AND/OR ENDOLYSINS

(71) Applicant: Eligo Bioscience, Paris (FR)

(72) Inventors: Antoine Decrulle, Paris (FR); Xavier Duportet, Paris (FR)

(73) Assignee: Eligo Bioscience, Paris (FR)

( * ) Notice: Subject to any disclaimer, the term of this patent is extended or adjusted under 35 U.S.C. 154(b) by 0 days.

(21) Appl. No.: 18/063,267

(22) Filed: Dec. 8, 2022

(65) Prior Publication Data

US 2023/0210961 A1 Jul. 6, 2023

Related U.S. Application Data

(62) Division of application No. 17/698,091, filed on Mar. 18, 2022, now Pat. No. 11,541,106.

(Continued)

(51) Int. Cl.
*A61K 35/747* (2015.01)
*A61K 38/47* (2006.01)
(Continued)

(52) U.S. Cl.
CPC ............ *A61K 38/47* (2013.01); *A61K 9/0014* (2013.01); *A61K 9/107* (2013.01); *A61K 35/74* (2013.01); *A61K 35/747* (2013.01); *A61K 38/164* (2013.01); *A61K 45/06* (2013.01); *A61P 17/00* (2018.01)

(58) Field of Classification Search
CPC .................................................... A61K 35/747
See application file for complete search history.

(56) References Cited

U.S. PATENT DOCUMENTS 8,568,714 B2   10/2013   Donovan et al.
2002/0187136 A1   12/2002   Loomis et al.
(Continued)

FOREIGN PATENT DOCUMENTS

CN      103119158 B      4/2015
WO      2013/153358 A1   10/2013
(Continued)

OTHER PUBLICATIONS

Liu et al., "Inhibition of *Staphylococcus aureus* by lysostaphin-expressing Lactobacillus plantarum WCFS1 in a modified genital tract secretion medium, Applied and Environmental Microbiology," 77(24):8500-8508, 2011.*
(Continued)

*Primary Examiner* — Rosanne Kosson
(74) *Attorney, Agent, or Firm* — Arrigo, Lee, Guttman & Mouta-Bellum LLP

(57) ABSTRACT

The present invention concerns a postbiotic composition comprising at least one postbiotic and at least one bacteriocin and/or endolysin, preferably formulated, and a postbiotic composition comprising at least one postbiotic and at least one bacteriocin and/or endolysin for use as a medicament, wherein said postbiotic is preferably a microbial lysate, preferably obtained from microorganisms heterologously expressing said at least one bacteriocin and/or endolysin and wherein said at least one postbiotic and said at least one bacteriocin and/or endolysin have a synergistic effect in the therapeutic treatment.

13 Claims, 8 Drawing Sheets

Specification includes a Sequence Listing.

Related U.S. Application Data

(60) Provisional application No. 63/163,083, filed on Mar. 19, 2021, provisional application No. 63/184,389, filed on May 5, 2021.

(51) Int. Cl.
*A61P 17/00* (2006.01)
*A61K 35/74* (2015.01)
*A61K 38/16* (2006.01)
*A61K 9/00* (2006.01)
*A61K 9/107* (2006.01)
*A61K 45/06* (2006.01)

(56) References Cited

U.S. PATENT DOCUMENTS

| | | |
|---|---|---|
| 2018/0325968 A1 | 11/2018 | Morris |
| 2019/0374621 A1 | 12/2019 | Offerhaus et al. |
| 2020/0254064 A1 | 8/2020 | Chumburidze |
| 2021/0244669 A1 | 8/2021 | O'Neill |
| 2022/0296499 A1 | 9/2022 | DeCrulle et al. |

FOREIGN PATENT DOCUMENTS

| | | |
|---|---|---|
| WO | 2015/005787 A1 | 1/2015 |
| WO | 2015/181534 A1 | 12/2015 |
| WO | 2017/199022 A2 | 11/2017 |

OTHER PUBLICATIONS

Turner et al. Antimicrobial activity of lysostaphin and a Listeria monocytogenes bacteriophage endolysin produced and secreted by lactic acid bacteria. Systematic and Applied Microbiology, 2007, 30(1), 58-67.

USPTO, Office Action in U.S. Appl. No. 17/698,075, dated Aug. 8, 2022,1-9.

Aguilar-Toala et al. Postbiotics: An evolving term within the functional foods field. Trends in Food Science & Technology, 2018, 75, 105-114.

Jung et al. Lysates of a Probiotic, Lactobacillus rhamnosus, Can Improve Skin Barrier Function in a Reconstructed Human Epidermis Model. International Journal of Molecular Sciences, 2019, 20(17), 4289. 1-12.

Khaneghah et al. Interaction between probiotics and pathogenic microorganisms in hosts and foods: A review. Trends in Food Science and Technology, 2020, 95, 205-218.

Mohammedsaeed et al. Lactobacillus rhamnosus GG Inhibits the Toxic Effects of *Staphylococcus aureus* on Epidermal Keratinocytes. Applied and Environmental Microbiology, 2014, 80(18), 5773-5781.

Salminen et al. The International Scientific Association of Probiotics and Prebiotics (ISAPP) consensus statement on the definition and scope of postbiotics. Reviews: Gastroenterology and Hepatology, 2021, 18, 649-667.

Totte et al. Successful Treatment of Chronic *Staphylococcus aureus*-Related Dermatoses with the Topical Endolysin Staphefekt SA. 100: A Report of 3 Cases. Case Reports in Dermatology, 2017, 9, 19-25.

Allain, Thibault et al. A new lactobacilli in vivo expression system for the production and delivery of heterologous proteins at mucosal surfaces, FEMS Microbiology Letters, 2016, 363(13), 1-9.

Bouslimani, Amina et al. Molecular catography of the human skin surface in 3D. PNAS, 2015, 112 (17), E2120-E2129.

Brachkova, M.I. et al. Alginate films containing Lactobacillus plantarum as wound dressing for prevention of burn Infection. Journal of Hospital Infection, 2011, 79(4), 375-377.

Briers, Yves et al. A standardized approach for accurate quantification of murein hydrolase activity in high throughput assays. Journal of Biochemical and Biophysics Methods, 2007, 70(3), 531-533.

Byrd, Allyson et al. The Human Skin Microbiome. Nature Reviews Microbiology, 2018, 16, 143-155. https://doi.org/10.1038/nrmicro.2017.157.

Chrowdhury, Sreyan et al. Programmable bacteria induce durable tumor regression and systemic antitumor immunity. Nature Medicine, 2019, 25(7), 1057-1063. https://doi.org/10.1038/s41591-019-0498-z.

Cotter, Paul. Bacteriocins: Developing innate immunity for food. Nature Reviews Microbiology, 2005, 3 (10), 777-788. doi:10.1038/nrmicro1240.

Donovan, David M et al. Lysis of staphylococcal mastitis pathogens by baeteriophage phi11 endolysin. FEMS Microbiol Lett, 2006, 265(1), 133-139. doi: 10.1111/j.1574-6968.2006.00483.x.

Fernandez-Ruiz, Iris et al. Thousands of novel endolysins discovered in uncultured phage genomes. Frontiers in Microbiology, 2018, 9, 1033, 1-8. https://doi.org/10.3389/fmicb.2018.01033.

Gervasi, T et al. Application of Lactobacillus johnsonii expressing phage endolysin for control of Clostridium perfringens. Letter's in Applied Microbiology, 2014, 59, 355-361.

Gervasi, Teresa et al. Expression and delivery of an endolysin to combat Clostridium perfringens. Applied Microbiology Biotechnology, 2014, 98, 2495-2505. DOI 10.1007/s00253-013-5128-.

Grice, E. et al. Topographical and temporal diversity of the human skin microbiome. Science, 2009, 324(5931), 1190-1192. doi:10.1126/science.1171700.

Gurbatri, Candice et al. Engineered probiotics for local tumor delivery of checkpoint blockade nanobodies. Sci Transl Med. 2020, 12(530), 1-26. doi:10.1126/scitranslmed.aax0876.

Heenan, C.N., Growth medium for culturing probiotic bacteria for applications in vegetarian food products. LWT Food Science and Technology, 2002, 35, 171-176.

Kong, Heidi H and Julia A Segre. Skin microbiome: looking back to move forward. Journal of Investigative Dermatology, 2012, 132, 933-939. doi: 10.1038/jid.2011.417.

Kurtz, Caroline et al. An engineered *E.coli* nissle improves hyperammonemia and survival in mice and shoes does-dependent exposure in healthy humans. Science Translational Medicine, 2019, 11, 1-14.

Leshem Avner et al. Immune-microbiota interplay and colonization resistance in infection. Molecular Cell, 2020, 78(4). 597-613.

Li, Nan W et al. Live and Heat-Killed Lactobacillus rhamnosus GG: Effects on Proinflammatory and Anti-Inflammatory Cytokines/Chemokines in Gastrostomy-Fed Infant Rats. Pediatric Research, 2009, 66 (2), 203-207.

Schmelcher et al. Bacteriophage Endolysins as Novel Antimicrobials, Future Microbiology, 2012, 7(10), 1147-1171.

Myers, Eugene and Webb Miller. Optimal alignments in linear space. Cabios, 1998, 4(1), 11-17.

Needleman, Saul B and Christian Wunsch. A general method applicable to the search for similarities in the amino acid sequence of two proteins. J. Mol. Biol, 1970, 48, 443-453.

Ohland, Christina L and Wallace K. MacNaughton. Probiotic bacteria and intestinal epithelial barrier function. Am J Physiol Gastrointest Liver Physiol, 2010, 298(6), G807-G819. doi:10.1152/ajpgi.00243.2009.

Peral, Maria C et al. Bacteriotherapy with Lactobacillus plantarum in burns. International Wound Journal, 2009, 6(1), 72-81.

Sorvig, Elisabeth et al. High-level, inducible gene expression in Lactobacillus sakei and Lactobacillus plantarum using versatile expression vectors. Microbiology, 2005, 151, 2439-2449. DOI 10.1099/mic.0.28084-0.

Suez, Jotham et al. The pros, cons, and many unknowns of probiotics. Nature Medicine, 2019, 25, 716-729.

USPTO, Office Action in U.S. Appl. No. 17/698,075, dated Nov. 29, 2022, 1-11.

Vargas Garcia, Cynthia et al. Piliation of Lactobacillus rhamnosus GG Promotes Adhesion, Phagocytosis, and Cytokine Modulation in Macrophages. Applied and Environmental Microbiology, 2015, 81(6), 2050-2062.

Lin, Yu-Tsan et al. Role of Bacterial Pathogens in Atopic Dermatitis. Clinic Rev Allerg Immunol, 2007, 33, 167-177. DOI 10.1007/s12016-007-0044-5.

(56) References Cited

OTHER PUBLICATIONS

Mohammedsaeed et al. Lactobacillus rhamnosus GG Lysate Increases Re-Epithelialization of Keratinocyte Scratch Assays by Promoting Migration. Scientific Reports, 2015, 5, 16147, 1-11.

Peral, M. C. et al. Interleukin-8 production by polymorphonuclear leukocytes from patients with chronic infected leg ulcers treated with Lactobacillus plantarum. Clinical Microbiology and Infection, 2010, 16(3), 281-286.

Sultana, Reshma et al. Strain-Dependent Augmentation of Tight-Junction Barrier Function in Human Primary Epiderm. Applied and Environmental Microbiology, 2013, 79 (16), 4887-4894.

Borysowski and Gorski. Anti-Staphylococcal Lytic Enzymes. Enzybiotics: Antibiotic Enzymes as Drugs and Therapeutics by Tomas G Villa Willey & Sons, 2010, Chapter 7, 149-172.

Liu H et al. Inhibition of *S. aureus* by Lysostaphin Expressing L. plantarum WCFS1 in a Modified Genital Tract Secretion Medium. Applied and Environmental Microbiology, 2011, 77(24), 8500-8508.

Esposito, C. Surface Level Happiness. 2020. 57(11), 62-66.

Meade, E. et al. Bacteriocins, Potent Antimicrobial Peptides and the Fight again Multi Drug Resistant Species: Resistance is Futile? Antibiotics, 2020, 9(32), 1-18.

Teame et al. Paraprobiotics and Postbiotics of Probiotic Lactobacilli, Their Positive Effects on the Host and Action Mechanisms: A Review. Frontiers in Nutrition, 2020, 7, 1-16.

Chang et al. Comparative Studies of Inhibitory and Antioxidant Activities, and Organic Acids Compositions of Postbiotics Produces by Probiotic Lactiplantibacillus plantarum Strains Isolated from Malaysian Foods. Frontiers in Veternary Science, 2021, 7, 1-14.

Abdelrahman F et al. Phage Encoded Endolysins Antibiotics, 2021, 10, 1-29.

Malashree L. et al. Postbiotics One Step Ahead of Probiotics. Int J Curr Micriobiol App Scie, 2019, 8(1), 2049-2053.

\* cited by examiner

THERAPEUTIC USE OF ENGINEERED POSTBIOTICS COMPRISING BACTERIOCINS AND/OR ENDOLYSINS

CROSS REFERENCE TO RELATED APPLICATIONS

This application is a divisional of U.S. application Ser. No. 17/698,091, filed on Mar. 18, 2022, which claims the benefit of U.S. application 63/163,083 filed Mar. 19, 2021, and U.S. application 63/184,389 filed May 5, 2021, which are herein incorporated by reference in their entirety.

TECHNICAL FIELD

The present invention relates to therapeutic methods for treating diseases associated with dysbiosis, in particular for treating inflammatory disorders, folliculitis or acne, and to pharmaceutical compositions suitable for such therapeutic methods.

BACKGROUND

The skin has a major role in protection from external aggressions such as environmental aggressions, climatic adversities (heat, cold, etc.), mechanical aggressions (epilation, shaving, abrasive scrubbing), chemical aggressions (detergents, pollutants, acids, etc.) and microbial pathogens. This property, called the barrier function, is primarily performed by the outermost layer of the epidermis, namely the horny layer or stratum corneum.

The skin also represents a complex ecosystem on which several types of microorganisms, such as bacteria, fungi, virus, proliferate. These microorganisms constitute the skin flora, also called skin microbiota.

The skin microbiota, made up of millions of commensal microorganisms (1 million/cm$^2$) is the second largest microbiota of the human body in mass (Byrd et al. (2018) Nat. Rev. Microbiol. 16:143-155). Cutaneous bacteria belong to four main phyla among the thirty-six known (Kong et al. (2012) J. Investig. Dermatol. 132:933-939). The average skin body distribution of these main bacteria phyla, detected on 20 diverse skin sites of 10 healthy individuals, were found to be *Actinobacteria* at 51.8%, *Firmicutes* at 24.4%, *Proteobacteria* at 16.5% and *Bacteroidetes* at 6.3% (Grice et al. (2009) Science 324:1190-1192; Bouslimani et al. (2015) Proc. Natl. Acad. Sci. 112:E2120-E2129).

Recent work suggests that skin commensal microorganisms are essential to maintaining healthy skin and maintaining the skin barrier. Commensal microorganisms are ones that are colonizing the host and part of the "normal" microbiota in opposition to pathogenic microorganisms. Recent focus on the normal microbiota revealed the beneficial role of commensal microorganisms on their host including in humans. Studies also suggest that certain skin diseases (such as acne vulgaris and atopic dermatitis) can be associated with disruptions to the normal microflora (Lin et al. (2007) Clin Rev Allergy Immunol 33(3): 167-177). More generally, many common skin disorders are postulated to have an underlying microbial contribution because clinical improvement is seen with antimicrobial treatments.

An important need thus exists for preventing and/or reversing such dysbiosis in order to treat or prevent such diseases of the skin.

Topical application of *Lactobacillus plantarum* has been demonstrated to improve tissue repair in a burned mouse model and prevent infection in chronic leg ulcers and burns in humans (Peral et al. (2009) Int Wound J 6(1):73-81; Peral et al. (2010) Clin Microbiol Infect 16(3): 281-286; Brachkova et al. (2011) J Hosp Infect 79(4): 375-377).

US20180325968 describes a product comprising a composition of prebiotic lipids and a composition containing probiotics such as *Bacillus licheniformis, Bifidobacterium breve, Bifidobacterium infantis, Lactobacillus fermentum, Lactobacillus plantarum, Lactobacillus rhamnosus, Lactobacillus sakei, Lactobacillus paracasei, Staphylococcus epidermidis*, and *Staphylococcus xylosus*, for correcting dysbiosis or for maintaining the balance of the resident beneficial commensal flora.

WO2015/005787 discloses a composition for skin treatment comprising an anti-inflammatory compound and a compound specifically targeting a bacterial cell such as *S. aureus*, said compound being typically an endolysin.

More generally, probiotics have started to be used to treat skin diseases because they seem to have a large panel of beneficial interactions with human health among which include:
- prevention or decrease of infection by pathogens through colonization resistance (Leshem et al. (2020) Mol Cell 78, 597-613; Cotter et al. (2005) Nat Rev Microbiol 3, 777-788);
- host immunomodulation (reviewed in Suez et al. (2019) Nat Med 25, 716-729);
- improved barrier function (reviewed in Ohland et al. (2010) Am J Physiol-gastr L 298, G807-G819); and
- potential modulation of host microbiota.

Because they have been used for years and are generally regarded as safe, they also have been engineered in order to increase their therapeutic potential by for example expressing cytokines (Allain et al. (2016) FEMS Microbiology Letters 363, fnw117), nanobodies (Gurbatri et al. (2020) Sci Transl Med 12, eaax0876; Chowdhury et al. (2019) Nat Med 25:1057-1063), enzymes (Kurtz et al. (2019) Sci Transl Med 11, eaau7975) or bacteriocins such as endolysins (Gervasi et al. (2014) Lett Appl Microbiol 59:355-361; Gervasi et al. (2014) Appl Microbiol Biot 98:2495-2505; Liu et al. (2011) Appl Environ Microb 77:8500-8508; Turner et al. (2007) Systematic and Applied Microbiology 30:58-67). However natural and engineered probiotics have several drawbacks due to their living characteristic:
- storage for long time requires complex formulation,
- containment strategies need to be put in place to prevent their survival in the host and in the environment,
- pharmacodynamics depends not only on the dose but also on the engraftment, even transitory, and metabolic state of the probiotic population, both parameters having high inter and intra individual variability.

Furthermore, many typical skin bacteria are potentially pathogenic (risk group 2), which clearly hampers their use as probiotics. Interestingly, many probiotics currently used for cosmetic purposes (lactic acid bacteria, Ammonia-Oxidizing Bacteria (AOB)) are classified as risk group 1 and are not typical members of the human skin microbiota, but often well-known probiotics from the intestinal tract. Nevertheless, topical application of such selected bacteria is thought to interfere with the colonization by other, potentially pathogenic, bacterial strains through competitive inhibition of binding sites, a mechanism defined as bacterial interference.

One way to circumvent inconveniences associated to probiotics is to directly administer the molecules, produced by the probiotics that act as the active substance:
- metabolic enzymes,
- metabolites,
- bacteriocins, bacterial structures (pili, flagels, cell wall components, DNA . . . )

Such molecules can be referred to as postbiotics.

These molecules can, in the case of secreted or freely diffusing molecules, be extracted from the media into which probiotics are growing. Examples of such molecules are Short Chain Fatty Acids (SOFA), vitamins and amino acids that are already well known microbial molecules with potential benefits for human health. This set of molecules is often referred to as cell-free supernatant (CFS). Other intracellular molecules can be extracted directly from the lysis of probiotic cells (lysate) or kept inside the inactivated (non-living) probiotic cells.

The present invention arises from the unexpected finding by the inventors that combining the beneficial effects of probiotics with their potential to produce recombinant molecules (here heterologously expressing bacteriocins and/or endolysins) led to synergistic activities particularly useful for therapeutic applications.

As an example, the present inventors engineered *Lactobacillus* bacteria to produce a bacteriocin targeting specifically the bacteria *S. aureus*, and showed that a lysate produced from the mechanical disruption of these engineered probiotic cells (corresponding to an engineered postbiotic) led to highly specific and efficient lysis of *S. aureus* strains without killing commensal species and even while promoting growth of commensal species. More importantly, compared to bacteriocin alone this engineered postbiotic leads to:
- a higher killing efficiency,
- a faster regrowth of commensal species,
- induction of an anti inflammatory response, and thus potentially to a de-escalation of inflammation-associated symptoms,
- a promotion of wound healing, thereby improving barrier function of the skin, and
- potentially a faster return to a healthy microbiota.

Thus engineered postbiotics offer a promising alternative to treat dysbiosis by specifically killing pathogenic microorganisms while at the same time promoting the growth of healthy commensal microorganisms.

SUMMARY OF THE INVENTION

The present invention thus concerns a postbiotic composition comprising at least one postbiotic and at least one bacteriocin and/or endolysin, preferably formulated, and a postbiotic composition comprising at least one postbiotic and at least one bacteriocin and/or endolysin for use as a medicament, wherein said at least one postbiotic and said at least one bacteriocin and/or endolysin have a synergistic effect in the therapeutic treatment. In a particular embodiment, said postbiotic is obtained from microorganisms, in particular bacteria, heterologously expressing said at least one bacteriocin and/or endolysin. In other words, in that embodiment, said at least one bacteriocin and/or endolysin included in said postbiotic composition is part of said postbiotic. In a particular embodiment, said postbiotic comprises a microbial, in particular bacterial, lysate, preferably obtained from microorganisms, in particular bacteria, heterologously expressing said at least one bacteriocin and/or endolysin and said microbial, in particular bacterial, lysate and said at least one bacteriocin and/or endolysin have a synergistic effect in the therapeutic treatment. In other words, in the embodiment wherein the engineered postbiotic comprises at least one microbial lysate obtained from microorganisms heterologously expressing said at least one bacteriocin and/or endolysin, said at least one bacteriocin and/or endolysin included in said postbiotic composition is part of said microbial lysate.

The present invention also concerns a postbiotic composition comprising at least one postbiotic and at least one bacteriocin and/or endolysin for use for treating an inflammatory disorder in a subject, wherein said at least one postbiotic and said at least one bacteriocin and/or endolysin have a synergic effect in the treatment of the inflammatory disorder in said subject. In a particular embodiment, said postbiotic is obtained from microorganisms, in particular bacteria, heterologously expressing said at least one bacteriocin and/or endolysin. In other words, in that embodiment, said at least one bacteriocin and/or endolysin included in said postbiotic composition is part of said postbiotic. In a particular embodiment, said postbiotic comprises a microbial, in particular bacterial, lysate, preferably obtained from microorganisms, in particular bacteria, heterologously expressing said at least one bacteriocin and/or endolysin and said microbial, in particular bacterial, lysate and said at least one bacteriocin and/or endolysin have a synergistic effect in the treatment of the inflammatory disorder in said subject. In other words, in the embodiment wherein the engineered postbiotic comprises at least one microbial lysate obtained from microorganisms heterologously expressing said at least one bacteriocin and/or endolysin, said at least one bacteriocin and/or endolysin included in said postbiotic composition is part of said microbial lysate.

Another object of the invention concerns a postbiotic composition comprising at least one postbiotic and at least one bacteriocin and/or endolysin for use for treating folliculitis in a subject, wherein said at least one postbiotic and said at least one bacteriocin and/or endolysin have a synergistic effect in the treatment of folliculitis in the subject. In a particular embodiment, said postbiotic is obtained from microorganisms, in particular bacteria, heterologously expressing said at least one bacteriocin and/or endolysin. In other words, in that embodiment, said at least one bacteriocin and/or endolysin included in said postbiotic composition is part of said postbiotic. In a particular embodiment, said postbiotic comprises a microbial, in particular bacterial, lysate, preferably obtained from microorganisms, in particular bacteria, heterologously expressing said at least one bacteriocin and/or endolysin and said microbial, in particular bacterial, lysate and said at least one bacteriocin and/or endolysin have a synergistic effect in the treatment of folliculitis in the subject. In other words, in the embodiment wherein the engineered postbiotic comprises at least one microbial lysate obtained from microorganisms heterologously expressing said at least one bacteriocin and/or endolysin, said at least one bacteriocin and/or endolysin included in said postbiotic composition is part of said microbial lysate.

The present invention further concerns a postbiotic composition comprising at least one postbiotic and at least one bacteriocin and/or endolysin for use for treating acne in a subject, wherein said postbiotic and said at least one bacteriocin and/or endolysin have a synergistic effect in the treatment of acne in said subject. In a particular embodiment, said postbiotic is obtained from microorganisms, in particular bacteria, heterologously expressing said at least one bacteriocin and/or endolysin. In other words, in that embodiment, said at least one bacteriocin and/or endolysin included in said postbiotic composition is part of said postbiotic. In a particular embodiment, said postbiotic comprises a microbial, in particular bacterial, lysate, preferably obtained from microorganisms, in particular bacteria, heterologously expressing said at least one bacteriocin and/or endolysin and said microbial, in particular bacterial, lysate and said at least one bacteriocin and/or endolysin have a synergistic effect in the treatment of acne in said subject. In other words, in the embodiment wherein the engineered postbiotic comprises at least one microbial lysate obtained from microorganisms heterologously expressing said at least one bacteriocin and/or endolysin, said at least one bacteriocin and/or endolysin included in said postbiotic composition is part of said microbial lysate.

Another object of the invention concerns a postbiotic composition comprising at least one postbiotic and at least one bacteriocin and/or endolysin for use for treating atopic dermatitis in a subject, wherein said at least one postbiotic and said at least one bacteriocin and/or endolysin have a synergistic effect in the treatment of atopic dermatitis in the subject. In a particular embodiment, said postbiotic is obtained from microorganisms, in particular bacteria, heterologously expressing said at least one bacteriocin and/or endolysin. In other words, in that embodiment, said at least one bacteriocin and/or endolysin included in said postbiotic composition is part of said postbiotic. In a particular embodiment, said postbiotic comprises a microbial, in particular bacterial, lysate, preferably obtained from microorganisms, in particular bacteria, heterologously expressing said at least one bacteriocin and/or endolysin and said microbial, in particular bacterial, lysate and said at least one bacteriocin and/or endolysin have a synergistic effect in the treatment of atopic dermatitis in the subject. In other words, in the embodiment wherein the engineered postbiotic comprises at least one microbial lysate obtained from microorganisms heterologously expressing said at least one bacteriocin and/or endolysin, said at least one bacteriocin and/or endolysin included in said postbiotic composition is part of said microbial lysate. In a particular embodiment, said postbiotic is obtained from *Lactobacillus rhamnosus*, in particular from *Lactobacillus rhamnosus* GG. In a particular embodiment, said at least one bacteriocin and/or endolysin is lysostaphin. In a particular embodiment, said postbiotic comprises a bacterial lysate obtained from *Lactobacillus rhamnosus*, in particular *Lactobacillus rhamnosus* GG, bacteria heterologously expressing lysostaphin, and said lysate and said endolysin have a synergistic effect in the treatment of atopic dermatitis.

The present invention also relates to a formulation, in particular a pharmaceutical formulation, comprising:
(i) a postbiotic composition comprising at least one postbiotic and at least one bacteriocin and/or endolysin,
(ii) at least one pharmaceutically acceptable excipient and/or adjuvant selected from the group consisting of disintegrants, binders, bulking agents/fillers, lubricants, glidants, wetting agents, penetration/permeation enhancers, mucoadhesive agents, preservatives, antifoaming agents, suspending agents, viscosity modifying agents, coloring agents, antioxidants, and combinations thereof, and
(iii) optionally an additional therapeutically active agent.

In a particular embodiment, said postbiotic is obtained from microorganisms, in particular bacteria, heterologously expressing said at least one bacteriocin and/or endolysin. In other words, in that embodiment, said at least one bacteriocin and/or endolysin included in said postbiotic composition is part of said postbiotic. In a particular embodiment, said postbiotic comprises a microbial, in particular bacterial, lysate preferably obtained from microorganisms, in particular bacteria, heterologously expressing said at least one bacteriocin and/or endolysin. In other words, in the embodiment wherein the engineered postbiotic comprises at least one microbial lysate obtained from microorganisms heterologously expressing said at least one bacteriocin and/or endolysin, said at least one bacteriocin and/or endolysin included in said postbiotic composition is part of said microbial lysate. In a particular embodiment, said postbiotic is obtained from *Lactobacillus rhamnosus*, in particular from *Lactobacillus rhamnosus* GG, bacteria heterologously expressing lysostaphin. In a particular embodiment, said posbiotic comprises a bacterial lysate obtained from *Lactobacillus rhamnosus*, in particular *Lactobacillus rhamnosus* GG, bacteria heterologously expressing lysostaphin.

DETAILED DESCRIPTION

Engineered Postbiotic

In the context of the invention, a postbiotic composition comprising at least one postbiotic, in particular engineered postbiotic, and at least one bacteriocin and/or endolysin is used.

By "postbiotic" is meant herein non-viable microbial products or metabolic byproducts from probiotic microorganisms that have biologic activity in the host, or inactivated or killed probiotic microorganisms that have biologic activity in the host such as *Bifidobacterium longum* 35624, *Lactobacillus acidophilus* CL1285, *Lactobacillus casei* LBC80R, *Lactobacillus rhamnosus* CLR2, *Lactobacillus reuteri* DSM 17938, *Escherichia coli* Nissle 1917, *Lactobacillus reuteri* ATCC PTA 5289, *Lactobacillus rhamnosus* GG (such as *Lactobacillus rhamnosus* GG LrOs11721 deposited under the Budapest Treaty on Mar. 16, 2022 before CNCM (Collection Nationale de Cultures de Microorganismes, Institut Pasteur, 25 rue du Docteur Roux, 75724 Paris, France) under deposit number CNCM I-5833, or *Lactobacillus rhamnosus* GG ATCC 53103), *Lactobacillus rhamnosus* GR-1, *Lactobacillus reuteri* RC-14, *Lactobacillus crispatus* LbV 88, *Lactobacillus jensenii* LbV 116, *Lactobacillus gasseri* LbV 150N, *Lactobacillus rhamnosus* LbV 96, *Lactobacillus plantarum* NCIMB 1193 or *Bifidobacterium animalis subsp. lactis* Bb12.

In a preferred embodiment, said postbiotic is an engineered postbiotic, i.e. a postbiotic obtained from an engineered probiotic microorganism.

The postbiotic composition used in the context of the invention comprises at least one postbiotic, in particular engineered postbiotic, and at least one bacteriocin and/or endolysin, in particular at least two, at least three, at least four, at least five or at least ten bacteriocin and/or endolysin. In a particular embodiment, the postbiotic composition used in the context of the invention comprises at least one postbiotic, in particular engineered postbiotic, at least two bacteriocins and/or endolysins.

By "bacteriocin" is meant herein a proteinaceous or peptidic toxin produced by bacteria to inhibit the growth of similar or closely related bacterial strain(s).

Bacteriocins are categorized in several ways, including producing strain, common resistance mechanisms, and mechanism of killing. Such bacteriocins have been described from gram negative bacteria (e.g. microcins, colicin-like bacteriocins and tailocins) and from gram positive bacteria (e.g. Class I, Class II, Class III or Class IV bacteriocins).

In one embodiment, said at least one bacteriocin is selected from the group consisting of microcins, colicin-like bacteriocins, tailocins, Class I, Class II, Class III and Class IV bacteriocins.

By "microcins" is meant herein very small bacteriocins, composed of relatively few amino acids, and typically including microcin V (MccV) produced by *Escherichia coli* and subtilosin A produced by *Bacillus subtilis*. Examples of microcins include MccB17, MccC, MccD93, MccJ25, MccL, MccV, MccS, MccE492, MccM, MccH47, Mccl47, MccN and MccPDI.

By "colicin-like bacteriocin" or "CLBs" is meant herein bacteriocins found in Gram-negative bacteria, which are modular proteins between 20 and 90 kDa in size and often consist of a receptor binding domain, a translocation domain and a cytotoxic domain. Examples of CLBs typically include colicins, in particular colicins A, B, D, K, E1, E2, E3, E4, E5, E6, E7, E8, E9, Ia, Ib, M, N, S4, U, Y, 5, 10; klebicins, in particular klebicins A, B, C, CCL, D, KpneA, KaerA, KoxyY, Kvarla, Kpnela, KaerM, KpneM (or Kpne CHS110), KpneM2 (or Kpne e1602) and KvarM (or Kvar 6A2); alveicins, in particular alveicins A and B; marcescins, in particular marcescins A, B and 28B; S-type pyocins, in particular pyocins S1, S2, S3, S5, S4, AP41; cloacins, in particular cloacin DF13; and pesticin.

By "tailocin" is meant herein a multisubunit bacteriocin that resembles bacteriophage tails. There are two classes of tailocin particles, the flexible noncontractile F-tailocins and the rigid contractile R-tailocins, which resemble and are evolutionarily related to *Siphoviridae* and *Myoviridae* phage tails, respectively. Examples of tailocins typically include F-type and R-type pyocins, carotovoricin, xenorhabdicin, and maltocin.

As used herein, the term "Class I bacteriocin" refers to small peptide inhibitors which include nisin and other lantibiotics. Examples of Class I bacteriocins typically include type A lantibiotics such as nisin A, nisin Z, bisin, subtilin, epidermin, gallidermin, mutacin II, mutacin I, mutacin III, pep5, epicidin 280, epilancin K7, lacticin 481, lacticin 3147, cytolysin, staphylococcin C55, salvaricin A, lactocin S, streptococcin A-FF2, sublancin 168, carnocin U149, variacin 8 and cypemycin; and type B lantibiotics such as mersacidin, actagardine, duramycin B, duramycin C, cinnamycin, ancovenin, and plantaricin C.

As used herein, the term "Class II bacteriocin" refers to small (<10 kDa) heat-stable bacteriocins, subdivided into five subclasses: the class IIa bacteriocins (pediocin-like bacteriocins), which correspond to the largest subgroup and contain an N-terminal consensus sequence across this group and a C-terminal region responsible for species-specific activity, causing cell-leakage by permeabilizing the target cell wall; the class IIb bacteriocins (two-peptide bacteriocins) which require two different peptides for activity; the class IIc bacteriocins which encompass cyclic peptides, in which the N-terminal and C-terminal regions are covalently linked; the class IId bacteriocins which cover single-peptide bacteriocins, which are not post-translationally modified and do not show the pediocin-like signature; and the class IIe bacteriocins, which encompass those bacteriocins composed of three or four non-pediocin like peptides. Examples of class IIa bacteriocins typically include pediocin, pediocin A, pediocin AcH, pediocin PA-1, pediocin PP-1, pediocin SJ-1, prepediocin AcH, prepediocin PA-1, mesentericin Y105, mesentericin 52A, carnobacteriocin B2, carnobacteriocin BM1, sakacin A, sakacin G, sakacin P, sakacin X, enterocin A, enterocin BC25, enterocin P, enterocin P-like, enterocin CRL35, enterocin HF, enterocin SE-K4, leucocin A, leucocin B-Ta11a, leucocin C, leucocin C-TA33a, curvacin A, listeriocin 743A, avicin A, bavaricin A/SppA, curvaticin L442, mundticin, mundticin CRL35, mundticin KS, mundticin L, mundticin QU2, pediocin ACCEL, piscicocin CS526, piscicolin 126, piscicolin 126, piscicocin V1a, bifidocin B, CoaA/Coagulin/CoaA, mutacin F-59.1, PapA, weissellin A, bacteriocin 602, bavaricin MN, divercin V41, divergicin M35, duracin GL, bacteriocin 31/BacA, bacteriocin 1580, bacteriocin 43, bacteriocin RC714, bacteriocin T8, hiracin JM79, penocin A/PenA, bacteriocin MC4-1, carnocin CP52, plantaricin 423, plantaricin C19, prebacteriocin SkgA2, lactococcin MMFII, ubericin A, piscicocin V1b, bacteriocin E50-52, bacteriocin L-1077, bacteriocin 37, acidocin A, and bacteriocin OR-7. Examples of class IIb bacteriocins typically include enterocin C, enterocin 1071, gassericin T, gassericin S, lactococcin G, lactococcin Q, plantaricin E/F, plantaricin J/K, plantaricin S, plantaricin NCB, lactacin F, brochocin-C, thermophilin 13, ABP-118, salivaricin P, mutacin IV and lactocin 705. Examples of class IIc bacteriocins typically include enterocin AS-48, lactocyclicin Q, garvicin ML, gassericin A, acidocin B and butyrovibriocin AR10. Examples of class IId bacteriocins typically include aureocin A53, garvicin A, laterosporulin10, lactococcin A, lactococcin 972, lacticin Q, carnobacteriocin XY, leucocin B, thuricin S, thuricin-17 and bactofensin A. Examples of class IIe bacteriocins typically include aureocin A70.

As used herein, the term "Class III bacteriocin" refers to large (>10 kDa), heat-labile protein bacteriocins. This class is subdivided in two subclasses: subclass IIIa (bacteriolysins) and subclass IIIb. Subclass IIIa comprises those peptides that kill bacterial cells by cell wall degradation, thus causing cell lysis, and typically include lysostaphin. Subclass IIIb, in contrast, comprises those peptides that do not cause cell lysis, killing the target cells by disrupting plasma membrane potential. Examples of class III bacteriocins typically include lysostaphin, enterolysin A, helveticin V-1829, helveticin J, caseicin 80, lactacin A, lactacin B, zoocin A, millericin B, linocin M18 and acidophilus A.

As used herein, the term "Class IV bacteriocin" refers to complex bacteriocins containing lipid or carbohydrate moieties. Examples of class IV bacteriocins typically include sublancin 168, glycocin F, ASM1, enterocin 96 and enterocin F4-9.

In a particular embodiment, said at least one bacteriocin and/or endolysin is a bacteriocin as defined above, more particularly a Class III bacteriocin as defined above, more particularly lysostaphin.

By "Lysostaphin" is meant herein a *Staphylococcus simulans* metalloendopeptidase, typically of sequence SEQ ID NO: 1, which specifically targets *Staphylococcus aureus*. In the context of the invention, the term "Lysostaphin" further encompasses any modified lysostaphin or variant of lysostaphin. In a particular embodiment, said lysostaphin comprises or consists of an amino acid sequence at least 80% identical, preferably at least 85%, at least 90%, at least 95% or at least 99% identical to the sequence SEQ ID NO: 1.

As used herein, the percent identity is calculated in relation to polymers (e.g., polynucleotide or polypeptide) whose sequences have been aligned. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W.

Miller (Comput. Appl. Biosci., 4: 11-17 (1988)) which has been incorporated into the ALIGN program (version 2.0), using a PAM 120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using a BLOSUM62 matrix, a BLOSUM30 matrix or a PAM250 matrix, and a gap weight of 16, 14, 12, 10, 8, 6, or 4 and a length weight of 1, 2, 3, 4, 5, or 6. In a specific embodiment the BLOSUM30 matrix is used with gap open penalty of 12 and gap extension penalty of 4.

By "endolysin" or "lysin" is meant herein enzymes used by bacteriophages at the end of their replication cycle to degrade the peptidoglycan of the bacterial host from within, resulting in cell lysis and release of progeny virions. They are typically either β(1,4)-glycosylases (lysozymes), transglycosylases, amidases or endopeptidases. Examples of endolysins typically include PhiV10p30, STM0907.Fels0, epsilon15p25, YuA20, ORF23, BcepMu22, F116p62, STM2715.S.Fels2, gp76, SPSV3_gp23, phi32_17, HK022p54, HK97p58, HK620p36, VIP0007, Sf6p62, R (SfVp40), gp22, Nazgul38, K (P2p09), K (Wphi09), rv5_gp085, EpJS98_gp116, gp3.5 (from 13A phage), gp3.5 (from BA14 phage), gp3.5 (from ECODS1 phage), CKV1F_gp16, T3p18, gh-1p12, gp3.5 (from K11 phage), ORF12, Bcep43-27, Bcep781-27, Bcep1-28, BcepNY3gene26, gp45, gp28, P27p30, RB49p102, phi1-p102, lys (T5.040), Aeh1p339, YYZgp45, φSH2 lysin, lysin from STB12 phage, PlyP40, endolysin from phi11 phage, endolysins from the *Pseudomonas aeruginosa* phages DKZ and EL, endolysins of the *Pseudomonas putida* phage, endolysins of the *E. coli* phage N4, endolysins of the phage LUZ24, gp61 muramidase, STM0016 endolysin, PSP3 endolysin, phiKZgp144, ELgp188, *Salmonella* endolysin, *Enterobacteria* phage T4 endolysin, *Acinetobacter baumanii* endolysin, *E. coli* phage KIF endolysin, OBPgpLYS, PS3 *Salmonella* endolysin (PSP3gp1), *E. coli* phage P2 endolysin (P2gp9), *Salmonella typhimurium* phage muramidase STM0016, *E. coli* phage N4 muramidase N4-gp61 and KZ144. Examples of endolysins also include endolysins disclosed in Fernandez-Ruiz et al. (2018) Front. Microbiol. 9:1033.

In a particular embodiment, the endolysin is encoded by bacteriophages specific for Gram-negative bacteria such as Enterobacteriaceae (*Escherichia*, especially *E. coli, Salmonella, Shigella, Citrobacter, Edwardsiella, Enterobacter, Hafnia, Klebsiella*, especially *K. pneumoniae, Morganella, Proteus, Providencia, Serratia, Yersinia*), Pseudomonadaceae (*Pseudomonas*, especially *P. aeruginosa, Burkholderia, Stenotrophomonas, Shewanella, Sphingomonas, Comamonas*), *Neisseria, Moraxella, Vibrio, Aeromonas, Brucella, Francisella, Bordetella, Legionella, Bartonella, Coxiella, Haemophilus, Pasteurella, Mannheimia, Actinobacillus, Gardnerella,* Spirochaetaceae (*Treponema* and *Borrelia*), Leptospiraceae, *Campylobacter, Helicobacter, Spirillum, Streptobacillus,* Bacteroidaceae (*Bacteroides, Fusobacterium, Prevotella, Porphyromonas*), *Acinetobacter*, especially *A. baumanii*.

In the context of the invention, said at least one bacteriocin and/or endolysin may be a wild-type bacteriocin and/or endolysin or an engineered bacteriocin and/or endolysin, in particular a bacteriocin and/or endolysin mutant, variant or chimera, typically comprising modifications and/or alterations of the amino acid sequence. Such alterations and/or modifications may comprise mutations such as deletions, insertions and additions, substitutions or combinations thereof and/or chemical changes of the amino acid residues, e.g. biotinylation, acetylation, pegylation, chemical changes of the amino-, SH- or carboxyl-groups. Such modified bacteriocin and/or endolysin typically exhibit the lytic activity of the respective wild-type bacteriocin and/or endolysin. However, said activity can be the same, higher or lower than the activity of the respective wild-type bacteriocin and/or endolysin. Said activity can be about 10, 20, 30, 40, 50, 60, 70, 80, 90, 100, 110, 120, 130, 140, 150, 160, 170, 180, 190 or about 200% of the activity of the respective wild-type bacteriocin and/or endolysin or even more. The activity can be measured by assays well known in the art by a person skilled in the art as e.g. the plate lysis assay or the liquid lysis assay which are e.g. described in Briers et al. (2007) J. Biochem. Biophys Methods 70:531-533, or Donovan et al. (2006) FEMS Microbiol Lett. 265:133-139.

In a particular embodiment, said at least one bacteriocin and/or endolysin targets at least one commensal bacterial species of the subject to be treated.

By "commensal bacterial species of the subject to be treated" is meant herein bacteria commonly associated with a healthy state of a microbiome in a particular niche of the subject to be treated, e.g., the gastrointestinal tract or the skin, and/or are generally considered non-pathogenic.

Commensal bacterial species in a particular niche of a subject to be treated are well-known from the skilled person.

Skin commensal bacteria are typically bacteria of the *Actinobacteria* phylum in particular of the Corynebacteriaceae family, the Propionibacteriaceae family and the Micrococcaceae family; of the *Firmicutes* phylum, in particular of Staphylococaceae family, of Lactobacillales order and of Clostridiales order; or of the *Proteobacteria* phylum. Examples of skin commensal bacteria typically include those of the genus *Staphylococcus, Cutibacterium, Corynebacterium, Streptococcus, Micrococcus, Bacillus, Brevibacterium, Kocuria, Roseomonas, Paenibacillus, Acinetobacter, Dietza, Dermacoccus, Enhydrobacter, Pseudomonas, Paracoccus, Microbacterium, Sporosarcina, Brachybacterium, Lysinibacillus, Aerococcus, Brevundimonas, Okibacterium, Pantoea, Variovorax* most precisely *Staphylococcus epidermidis, Staphylococcus hominis, Staphylococcus capitis, Staphylococcus wameri, Staphylococcus haemolyticus, Cutibacterium acnes* (formerly called *Propionibacterium acnes*), *Cutibacterium avidum, Cutibacterium granulosum, Corynebacterium tuberculostearicum, Corynebacterium afermentans, Corynebacterium simulans, Corynebacterium resistens, Corynebacterium kroppenstedtii, Corynebacterium aurimucosum, Corynebacterium amycolatum, Streptococcus mitis, Streptococcus oralis, Streptococcus pseudo pneumoniae, Streptococcus sanguinis, Micrococcus luteus, Bacillus cereus, Bacillus subtilis, Brevibacterium epidermidis, Veillonella parvula, Enhydrobacter aerosaccus.*

In another embodiment, said at least one bacteriocin and/or endolysin targets at least one pathogenic bacterial species.

By "targeting a particular species" is meant herein that said bacteriocin and/or endolysin is able to recognize, preferably specifically recognize, a particular species, and to exert, preferably specifically exert, their bactericidal, bacteriostatic and/or lytic activity on said particular species.

By "specifically targets a particular species" is meant herein that said bacteriocin and/or endolysin bind to and/or exert their activity on said particular species but does not significantly bind to other species, and/or do not exert their activity on other species, in particular on commensal bacterial species, in a significant way, in particular to an extent which affects the use of said postbiotic, in particular engineered postbiotic, in therapeutic applications.

In a particular embodiment, said bacteriocin and/or endolysin specifically targets at least one pathogenic bacterial species, in particular by exerting its killing activity on said at least one pathogenic bacterial species, without killing commensal bacterial species. In a more particular embodiment, said bacteriocin and/or endolysin has a killing/reduction activity level on said at least one pathogenic bacterial species, at least 1 log, at least 2 log, at least 3 log or at least 4 log higher than on commensal bacterial species.

By "pathogenic bacterial species" is meant herein any bacteria that can cause and/or do cause a disease or condition in a subject. In some embodiments, the term includes pathogenic bacteria that colonize the skin and/or mucosa of a subject, the eye of a subject, the vagina of a subject, the lungs of a subject or the gut of a subject. In some embodiments, the term includes material that are pathogenic if present or overabundant on skin and/or mucosa of a subject, the eye of a subject, the vagina of a subject, the lungs of a subject or in the gut of a subject. In a more particular embodiment, the term includes material that are pathogenic if present or overabundant on skin and/or mucosa of a subject.

Examples of pathogenic bacterial species, in particular pathogenic bacterial species associated with skin and/or mucosa diseases or disorders, include *Staphylococcus* sp., in particular *S. aureus*; *Streptococcus* sp., in particular *S. pyogenes*; *Corynebacterium* sp., in particular *C. minutissimum*; *Erysipelothrix rhusiopathiae*; *Bacillus* sp., in particular *B. anthracis*; *Helicobacter* sp., in particular *H. cinaedi*; *Pseudomonas* sp., in particular *P. aeruginosa*; *Pasteurella multocida*; *Bartonella* sp., in particular *B. henselae, B. quintana* and *B. bacilliformis*; *Capnocytophaga canimorsus*; *Klebsiella* sp., in particular *K. rhinoscleromatis*; *Vibrio* sp., in particular *V. vulnificus*; *Chlamydia* sp.; *Clostridium* sp., in particular *C. perfringens*; *Haemophilus* sp., in particular *H. influenzae* and *H. parainfluenzae*; *Mycobacterium* sp.; *Mycoplasma* sp.; *Treponema* sp. and *Neisseria* sp.

Other examples of pathogenic bacterial species include *Bacillus* sp., in particular *B. cereus*; *Streptococcus* sp., in particular *S. agalactiae* and *S. pneumoniae*; *Salmonella* sp.; *Listeria* sp., in particular *L. monocytogenes* and *L. innocua*; *E. coli*; *Shigella* sp.; *Campylobacter* sp.; *Bartonella* sp.; *Bordetella* sp.; *Borrelia* sp.; *Brucella* sp.; *Enterococcus* sp., in particular *E. faecalis* and *E. faecium*; *Francisella* sp.; *Legionella* sp.; *Leptospira* sp.; *Mycobacterium* sp., in particular *M. tuberculosis*; *Rickettsia* sp. and *Yersinia* sp.

In a particular embodiment, the postbiotic composition of the invention comprises at least two, in particular at least three, at least four, at least five, or more different bacteriocins and/or endolysins. In particular, the postbiotic composition of the invention may comprise at least one bacteriocin and at least one endolysin. Alternatively, the postbiotic composition of the invention may comprise at least two bacteriocins. Alternatively, the postbiotic composition of the invention may comprise at least two endolysins. In a particular embodiment, the postbiotic composition of the invention comprises lysostaphin, and at least one other bacteriocin and/or endolysin.

In the embodiment wherein the postbiotic composition of the invention comprises at least two different bacteriocins and/or endolysins, said at least two different bacteriocins and/or endolysins may target the same bacterial species, in particular may target the same commensal or the same unfavorable and/or pathogenic bacterial species. Alternatively, in said embodiment, said at least two different bacteriocins and/or endolysins may target different bacterial species, in particular different commensal bacterial species, or different unfavorable and/or pathogenic bacterial species, or both commensal and unfavorable and/or pathogenic bacterial species.

In an embodiment of the invention, said at least one bacteriocin and/or endolysin is heterologously expressed by the microorganism, in particular by the bacteria, from which at least one postbiotic, in particular at least one engineered postbiotic, is obtained. Accordingly, in a particular embodiment, said at least one bacteriocin and/or endolysin is comprised in said at least one postbiotic, in particular in said at least one engineered postbiotic.

In a more particular embodiment of the invention, said at least one bacteriocin and/or endolysin is heterologously expressed by the microorganism, in particular by the bacteria, from which the at least one microbial, in particular bacterial, lysate, comprised in said at least one engineered postbiotic, is obtained. Accordingly, in a particular embodiment, said at least one bacteriocin and/or endolysin is comprised in said at least one microbial, in particular bacterial, lysate, comprised in said at least one engineered postbiotic.

As used herein, the term "heterologous" means derived from a different species or derived from a different organism.

The term "heterologous expression" means transcription and optionally translation of nucleotide sequences which are not native to the cell but which have been incorporated into the cell's chromosomal or extra-chromosomal expression system or as extra-chromosomal expression system, by genetic engineering techniques known in the art.

In a particular embodiment, said at least one bacteriocin and/or endolysin is not secreted by said microorganism, in particular said bacteria. Accordingly, in a particular embodiment, said at least one bacteriocin and/or endolysin is not present in the cell culture supernatant of said microorganism, in particular of said bacteria. In an alternative embodiment, said at least one bacteriocin and/or endolysin is secreted by said microorganisms, in particular said bacteria.

In a particular embodiment, said microorganism, in particular bacteria, in particular heterologously expressing said at least one bacteriocin and/or endolysin, is GRAS and/or probiotic microorganism, in particular bacteria.

By "GRAS microorganism" or "Generally Recognized as Safe microorganism" is meant herein microorganisms considered as safe by the FDA when added to food. Examples of GRAS microorganisms typically include *Bacillus cereus, Bacillus coagulans, Bacillus lentus, Bacillus licheniformis, Bacillus pumilus, Bacillus subtilis, Bacteroides amylophilus, Bacteroides capillosus, Bacteroides ruminocola, Bacteroides suis, Bifidobacterium adolescentis, Bifidobacterium animalis, Bifidobacterium bifidum, Bifidobacterium breve, Bifidobacterium infantis, Bifidobacterium lactis, Bifidobacterium longum, Bifidobacterium thermophilum, Escherichia coli* Nissle 1917, *Lactobacillus acidophilus, Lactobacillus brevis* (also called *Levilactobacillus brevis*), *Lactobacillus bulgaricus* (also called *Lactobacillus delbrueckii subsp. bulgaricus*), *Lactobacillus casei* (also called *Lacticaseibacillus casei*), *Lactobacillus cellobiosus, Lactobacillus curvatus* (also called *Latilactobacillus curvatus*), *Lactobacillus delbruekii, Lactobacillus fermentum* (also called *Limosilactobacillus fermentum*), *Lactobacillus gasseri, Lactobacillus johnsonii, Lactobacillus paracasei* (also called *Lacticaseibacillus paracasei*), *Lactobacillus plantarum* (also called *Lactiplantibacillus plantarum*), *Lactobacillus reuteri* (also called *Limosilactobacillus reuteri*), *Lactobacillus salivarius* (also called *Ligilactobacillus*

*salivarius*), *Lactococcus lactis, Leuconostoc mesenteroides, Pediococcus acidilacticii, Pediococcus cerevisiae, Pediococcus pentosaceus, Propionibacterium freudenreichii, Propionibacterium shermanii, Streptococcus cremoris, Streptococcus diacetylactis, Streptococcus faecium, Streptococcus intermedius, Streptococcus lactis* and *Streptococcus thermophilus*.

As used herein, "probiotic microorganisms" refer to living microorganisms which, when taken in adequate quantities, have a beneficial effect on the host organism. Probiotic microorganisms can comprise a non-pathogenic microbial population, e.g., an immunomodulatory bacterial population, such as an anti-inflammatory bacterial population. Probiotics include, but are not limited to lactobacilli, bifidobacteria, streptococci, enterococci, propionibacteria, saccharomycetes, proteobacteria, or saccharomyces. Examples of probiotic bacteria include, without limitation, strains of *Lactobacillus acidophilus, Lactobacillus casei* (also called *Lacticaseibacillus casei*), *Lactobacillus paracasei* (also called *Lacticaseibacillus paracasei*), *Lactobacillus rhamnosus* (also called *Lacticaseibacillus rhamnosus*), in particular *Lactobacillus rhamnosus* GG (such as *Lactobacillus rhamnosus* GG LrOs11721 deposited under the Budapest Treaty on Mar. 16, 2022 before CNCM (Collection Nationale de Cultures de Microorganismes, Institut Pasteur, 25 rue du Docteur Roux, 75724 Paris, France) under deposit number CNCM 1-5833, or *Lactobacillus rhamnosus* GG ATCC 53103), *Lactobacillus delbrueckii subsp. bulgaricus, Lactobacillus brevis* (also called *Levilactobacillus brevis*), *Lactobacillus johnsonii, Lactobacillus plantarum* (also called *Lactiplantibacillus plantarum*), *Lactobacillus fermentum* (also called *Limosilactobacillus fermentum*), *Lactobacillus reuteri* (also called *Limosilactobacillus reuteri*), *Bifidobacterium lactis* (in particular *Bifidobacterium lactis* DN-173 010), *Bifidobacterium animalis subsp. lactis, Bifidobacterium infantis, Bifidobacterium adolescentis, Bifidobacterium animalis subsp. animalis, Bifidobacterium animalis subsp. lactis, Bifidobacterium bifidum, Bifidobacterium longum, Bifidobacterium breve, Lactococcus lactis subsp. lactis, Enterococcus durans, Enterococcus faecium, Streptococcus thermophilus, Bacillus subtilis, Bacillus coagulans, Bacillus cereus, Pediococcus acidilactici, Leuconostoc mesenteroides* and *Escherichia coli*, in particular *E. coli* Nissle 1917. Examples of probiotic strains include *B. longum* 35624, *L. acidophilus* CL1285, *L. casei* LBC80R, *L. rhamnosus* CLR2, *L. reuteri* DSM 17938, *Escherichia coli* Nissle 1917, *L. reuteri* ATCC PTA 5289, *L. rhamnosus* GG (such as *L. rhamnosus* GG LrOs11721 deposited under the Budapest Treaty on Mar. 16, 2022 before CNCM (Collection Nationale de Cultures de Microorganismes, Institut Pasteur, 25 rue du Docteur Roux, 75724 Paris, France) under deposit number CNCM I-5833, or *L. rhamnosus* GG ATCC 53103), *L. rhamnosus* GR-1, *L. reuteri* RC-14, *L. crispatus* LbV 88, *L. jensenii* LbV 116, *L. gasseri* LbV 150N, *L. rhamnosus* LbV 96, *L. plantarum* NCIMB 1193, *B. lactis* Bb12. Examples of probiotic yeasts include *Saccharomyces boulardii* and *Saccharomyces cerevisiae*.

In a particular embodiment, said bacteria, in particular heterologously expressing said at least one bacteriocin and/or endolysin, as defined above, are *Lactobacillus* or *Escherichia* bacteria, more particularly bacteria selected from the group consisting of *Lactobacillus rhamnosus, Lactobacillus plantarum* and *Escherichia coli* bacteria.

In a particular embodiment, said bacteria, in particular heterologously expressing said at least one bacteriocin and/or endolysin, as defined above, are *Lactobacillus rhamnosus* bacteria, more particularly *Lactobacillus rhamnosus* GG bacteria (such as *Lactobacillus rhamnosus* GG LrOs11721 deposited under the Budapest Treaty on Mar. 16, 2022 before CNCM (Collection Nationale de Cultures de Microorganismes, Institut Pasteur, 25 rue du Docteur Roux, 75724 Paris, France) under deposit number CNCM 1-5833, or *Lactobacillus rhamnosus* GG ATCC 53103).

In a particular embodiment, said microorganisms, in particular bacteria, more particularly heterologously expressing said at least one bacteriocin and/or endolysin, as defined above, are obtained from microorganisms, in particular bacteria, isolated from a subject, in particular from the subject to be treated. In particular, said microorganisms, in particular bacteria, may be obtained from a subject's, more particularly the subject to be treated's, skin or gut microbiota, more particularly from a subject's, more particularly from the subject to be treated's, skin microbiota.

In the context of the invention, said microorganisms, in particular bacteria, heterologously expressing said at least one bacteriocin and/or endolysin, as defined above, have typically been genetically modified to express said at least one bacteriocin and/or endolysin.

Said microorganisms, in particular bacteria, can be genetically modified to express said at least one bacteriocin and/or lysostaphin by any suitable technique, well-known from the skilled person. For example, said bacteria can be genetically modified by transformation (chemical transformation or ultrasound transformation), transduction (using for example optionally engineered bacteriophages, or packaged phagemids technologies), conjugation, or electroporation.

In a particular embodiment, said microorganisms, in particular bacteria, more particularly said microorganisms, in particular bacteria, heterologously expressing said at least one bacteriocin and/or endolysin, as defined above, do not comprise any antibiotic resistance marker. Therefore, other types of selection markers, than antibiotic resistance markers, may be used when genetically modifying said microorganisms, in particular bacteria. For example, suitable selection markers include auxotrophic selection markers such as alr (alanine racemase), thyA (Thymidylate synthase), dapA (4-hydroxy-tetrahydrodipicolinate synthase). In a particular embodiment, said auxotrophic selection marker is alr. In another particular embodiment, said auxotrophic selection marker is thyA.

In a particular embodiment, said microorganisms, in particular bacteria, more particularly said microorganisms, in particular bacteria, heterologously expressing said at least one bacteriocin and/or endolysin, as defined above, do not comprise any antibiotic resistance marker and the bacteriocin expression cassette is integrated in the genome of said microorganisms, in particular bacteria, and no antibiotic resistance marker is present in the engineered microorganisms, in particular bacteria.

In a particular embodiment, the postbiotic, in particular engineered postbiotic, of the invention comprises a microbial, in particular bacterial, lysate.

As used herein, the term "microbial lysate" refers to the composition obtained after the destruction or dissolution of microbial cells via cell lysis which results in the release of the intracellular biological constituents contained in the microbial cells. Microorganisms, in particular bacteria, lysis may be accomplished via various techniques, such as an osmotic shock, a thermic shock, a heat-treatment (e.g., tyndallization), via ultrasonication, via high pressure, or alternatively under a mechanical stress of centrifugation type. In a particular embodiment, the microbial cell debris is removed prior to use. In more particular embodiments the microbial, in particular bacterial, lysates are filtered prior to use. In exemplary embodiments, the microbial, in particular bacterial, cells are lysed by, for example bead beating or high pressure homogenisation. In a particularly preferred embodiment, said bacterial lysate is a bacterial ferment lysate filtrate. In a particular embodiment, said microbial, in particular bacterial, lysate is not heat-inactivated.

By "bacterial ferment lysate" is meant herein a bacterial lysate, as defined above, obtained from bacteria after fermentation.

In a particular embodiment, said postbiotic, in particular said engineered postbiotic, acts as a prebiotic and/or has a beneficial effect on commensal microorganisms, in particular commensal bacteria. In a more particular embodiment, said microbial, in particular bacterial, lysate acts as a prebiotic and/or has a beneficial effect on commensal microorganisms, in particular commensal bacteria.

By "prebiotic" is meant herein an ingredient that allows specific changes, both in the composition and/or activity in the subject's microbiota that may confer benefits upon the subject.

In a particular embodiment, said postbiotic, in particular said microbial, more particularly bacterial, lysate stimulates growth of at least one commensal bacterial species, as defined above, of the subject.

In the embodiment wherein said postbiotic, in particular said microbial, more particularly bacterial, lysate acts as a prebiotic and/or has a beneficial effect on commensal microorganisms, more particularly stimulates growth of at least one commensal bacterial species, as defined above, of the subject, said at least one bacteriocin and/or endolysin, as defined above, may target at least one unfavorable and/or pathogenic bacterial species, as defined above.

In a particular embodiment, the at least one postbiotic, in particular engineered postbiotic, is constituted by the at least one microbial, in particular bacterial, lysate, as defined above, and the at least one bacteriocin and/or endolysin, as defined above, said at least one bacteriocin and/or endolysin being preferably part of the microbial, in particular bacterial, lysate.

In a particular embodiment, the postbiotic composition comprises a mixture of postbiotics, in particular of engineered postbiotics, preferably a mixture of microbial, in particular bacterial, lysates, as defined above.

In said particular embodiment, the postbiotic composition may comprise (i) a postbiotic, in particular an engineered postbiotic, preferably a microbial, in particular bacterial, lysate obtained from microorganisms, in particular bacteria, which heterologously express said at least one bacteriocin and/or endolysin, and (ii) at least one other postbiotic, preferably microbial, in particular bacterial, lysate obtained from microorganisms, in particular bacteria, which do not express any heterologous bacteriocin and/or endolysin, or which heterologously express another bacteriocin and/or endolysin.

In a particular embodiment, the postbiotic composition of the invention comprises a mixture of postbiotic, in particular microbial, in particular bacterial, lysate, as defined above, and of at least one isolated bacteriocin and/or endolysin, as defined above. By "mixture of postbiotic and of at least one isolated bacteriocin and/or endolysin" is meant herein that the at least one bacteriocin and/or endolysin was not expressed by the microorganisms from which the postbiotic is obtained, but was added to said postbiotic.

Therapeutic Use

The present invention concerns a postbiotic composition comprising at least one postbiotic, in particular engineered postbiotic, as defined in the section "Engineered postbiotic" above, and at least one bacteriocin and/or endolysin, as defined in the section "Engineered postbiotic" above, for use as a medicament, wherein said at least one postbiotic and said at least one bacteriocin and/or endolysin have a synergic effect in the therapeutic treatment. In a particular embodiment, said postbiotic, in particular engineered postbiotic, obtained from microorganisms, in particular bacteria, heterologously expressing said at least one bacteriocin and/or endolysin, as defined in the section "Engineered postbiotic" above. In a particular embodiment, said postbiotic, in particular engineered postbiotic, comprises a microbial, in particular bacterial, lysate, as defined in the section "Engineered postbiotic" above, preferably obtained from microorganisms, in particular bacteria, heterologously expressing said at least one bacteriocin and/or endolysin, as defined in the section "Engineered postbiotic" above, and said microbial, in particular bacterial, lysate and said at least one bacteriocin and/or endolysin have a synergistic effect in the therapeutic treatment.

The present invention also concerns a method for the therapeutic treatment of a subject in need thereof, comprising administering, to said subject in need thereof, a therapeutically effective amount of a postbiotic composition comprising at least one postbiotic, in particular engineered postbiotic, as defined in the section "Engineered postbiotic" above, and at least one bacteriocin and/or endolysin, as defined in the section "Engineered postbiotic" above, wherein said at least one postbiotic and said at least one bacteriocin and/or endolysin have a synergic effect in the therapeutic treatment. In a particular embodiment, said postbiotic, in particular engineered postbiotic, obtained from microorganisms, in particular bacteria, heterologously expressing said at least one bacteriocin and/or endolysin, as defined in the section "Engineered postbiotic" above. In a particular embodiment, said postbiotic, in particular engineered postbiotic comprises a microbial, in particular bacterial, lysate, as defined in the section "Engineered postbiotic" above, preferably obtained from microorganisms, in particular bacteria, heterologously expressing said at least one bacteriocin and/or endolysin, as defined in the section "Engineered postbiotic" above, and said microbial, in particular bacterial, lysate and said at least one bacteriocin and/or endolysin have a synergistic effect in the therapeutic treatment.

The present invention further concerns the use of a postbiotic composition comprising at least one postbiotic, in particular engineered postbiotic, as defined in the section "Engineered postbiotic" above, and at least one bacteriocin and/or endolysin, as defined in the section "Engineered postbiotic" above, for the manufacture of a medicament, wherein said at least one postbiotic and said at least one bacteriocin and/or endolysin have a synergic effect in the therapeutic treatment. In a particular embodiment, said postbiotic, in particular engineered postbiotic, obtained from microorganisms, in particular bacteria, heterologously expressing said at least one bacteriocin and/or endolysin, as defined in the section "Engineered postbiotic" above. In a particular embodiment, said postbiotic, in particular engineered postbiotic comprises a microbial, in particular bacterial, lysate, as defined in the section "Engineered postbiotic" above, preferably obtained from microorganisms, in particular bacteria, heterologously expressing said at least one bacteriocin and/or endolysin, as defined in the section "Engineered postbiotic" above, and said microbial, in particular bacterial, lysate and said at least one bacteriocin and/or endolysin have a synergistic effect in the therapeutic treatment.

As used herein, the terms "treatment", "treating," and the like, refer to obtaining a desired pharmacologic or physiologic effect. The effect may be therapeutic in terms of a partial or complete cure for a disease or disorder, or an adverse effect attributable to the disease or disorder. "Treatment" as used herein, covers any treatment of a disease or disorder in a mammal, particularly in a human, and can include inhibiting the disease or condition, i.e., arresting its development; and relieving the disease, i.e., causing regression of the disease.

As used herein, the term "prevention" includes preventing or decreasing the likelihood or severity of the onset of a disease. This includes prophylactic treatment of those having an enhanced risk of developing such disease. An elevated risk represents an above-average risk that a subject will develop a disease, which can be determined, for example, through family history, detection of genes causing a predisposition to developing said disease, or treatment with antibiotics.

The term "therapeutically effective amount" refers to a nontoxic but sufficient amount of an active agent to provide the desired therapeutic effect.

The subject according to the invention is an animal, preferably a mammal, even more preferably a human. However, the term "subject" can also refer to non-human animals, in particular mammals such as dogs, cats, horses, cows, pigs, sheeps, donkeys, rabbits, ferrets, gerbils, hamsters, chinchillas, rats, mice, guinea pigs and non-human primates, among others, that are in need of treatment or non mammals such as poultry.

The human subject according to the invention may be a new-born, a child, an infant, an adolescent or an adult at any age.

In a particular embodiment, the disease to be treated is a disease affecting the skin and/or the mucosa.

According to one embodiment of the present invention, the skin refers to the skin of the arms, especially the hands, the skin of the legs, especially the feet, the skin of the armpits, the skin of the neck, the skin of the chest, the skin of the back, the skin of the scalp, and/or the skin of the face, preferably the skin of the face.

As used herein, the term "mucosa" refers to a membrane that lines various cavities in the body or covers those surfaces. It is continuous with the skin at various body openings such as the eyes, ears, inside the nose, inside the mouth, lip, vagina, the urethral opening and the anus. Some mucous membranes secrete mucus. Mucosa typically include, e.g., oral mucosa, tongue, vaginal mucosa, nasal mucosa, and the anal canal.

By "synergistic effect" is meant a greater-than-additive effect that is produced by the combination of the postbiotic, preferably the microbial lysate and of the at least one bacteriocin and/or endolysin (optionally expressed by the microorganisms, in particular bacteria, from which said postbiotic, preferably microbial lysate is obtained) as compared to each of the postbiotic, preferably microbial lysate (obtained from microorganisms, in particular bacteria, which do not express said at least one bacteriocin and/or endolysin) and the at least one bacteriocin and/or endolysin alone. In some embodiments, synergy or synergistic effect refers to an advantageous effect of using the postbiotic, preferably microbial lysate and the at least one bacteriocin and/or endolysin (optionally expressed by the microorganisms, in particular bacteria, from which said postbiotic, preferably microbial lysate is obtained) in combination, e.g., in a pharmaceutical composition, or in a method of therapeutic treatment.

In a particular embodiment, said at least one postbiotic and said at least one bacteriocin and/or endolysin has a synergistic effect on killing and/or inhibiting the growth of the bacterial species targeted by said at least one bacteriocin and/or endolysin.

In a particular embodiment, the postbiotic composition, as defined in the section "Engineered postbiotic" above, comprising at least one postbiotic, as defined in the section "Engineered postbiotic" and at least one bacteriocin and/or endolysin, as defined in the section "Engineered postbiotic" above, is for use for treating an inflammatory disorder in a subject.

The present invention further concerns a method for treating an inflammatory disorder in a subject in need thereof, comprising administering, to said subject in need thereof, a therapeutically effective amount of a postbiotic composition, as defined in the section "Engineered postbiotic" above, comprising at least one postbiotic as defined in the section "Engineered postbiotic" above, and at least one bacteriocin and/or endolysin, as defined in the section "Engineered postbiotic" above, wherein said postbiotic and said at least one bacteriocin and/or endolysin have a synergistic effect in the treatment of inflammatory disorder in the subject.

Another object of the invention concerns the use of a postbiotic composition, as defined in the section "Engineered postbiotic" above, comprising at least one postbiotic, as defined in the section "Engineered postbiotic" above, and at least one bacteriocin and/or endolysin, as defined in the section "Engineered postbiotic" above, for the manufacture of a medicament intended to treat an inflammatory disorder, wherein said postbiotic and said at least one bacteriocin and/or endolysin have a synergistic effect in the treatment of inflammatory disorder.

By "inflammatory disorder" is meant herein any disease or disorder characterized by an abnormal and/or excessive inflammatory response. Inflammatory disorders include, without limitation, coronary artery disease, rheumatoid arthritis, osteoporosis, nephropathy in diabetes mellitus, alopecia areata, Graves' disease, systemic lupus erythematosus, lichen sclerosus, ulcerative colitis, periodontal disease, juvenile chronic arthritis, chronic iridocyclitis, psoriasis, insulin dependent diabetes, diabetic complications, diabetic retinopathy, atherosclerosis, metabolic syndrome, inflammatory bowel disease, Crohn's disease, non-alcoholic fatty liver disease, osteoarthritis, congestive heart failure, neurodegenerative diseases, multiple sclerosis, rosacea, asthma and any other diseases with an inflammatory component.

Said inflammatory disorder can typically be triggered, worsened or sustained by pro-inflammatory bacterial species.

Examples of pro-inflammatory bacterial species are well-known from the skilled person and typically include *Escherichia* sp., in particular *E. coli*; *Klebsiella* sp.; *Shigella* sp.; *Bacteroides* sp., in particular *B. fragilis*; and *Enterococcus* sp. Other examples of pro-inflammatory bacterial species typically include pathogenic bacterial species as defined above.

In the embodiment wherein the postbiotic composition of the invention is for use for treating an inflammatory disorder, said postbiotic composition may both have anti-inflammatory effect on said subject and target pro-inflammatory bacterial species, as defined above, of said subject.

By "anti-inflammatory effect" is meant herein the prevention of induction or reduction of induction of various pro-inflammatory cytokines and adhesion molecules.

In another particular embodiment, the postbiotic composition, as defined in the section "Engineered postbiotic" above, comprising at least one postbiotic, as defined in the section "Engineered postbiotic" above, and at least one bacteriocin and/or endolysin, as defined in the section "Engineered postbiotic" above, is for use for treating folliculitis in a subject.

The present invention further concerns a method for treating folliculitis in a subject in need thereof, comprising administering, to said subject in need thereof, a therapeutically effective amount of a postbiotic composition, as defined in the section "Engineered postbiotic" above, comprising at least one postbiotic, as defined in the section "Engineered postbiotic" above and at least one bacteriocin and/or endolysin, as defined in the section "Engineered postbiotic" above, wherein said at least one postbiotic and at least one bacteriocin and/or endolysin have a synergistic effect in the treatment of folliculitis in the subject.

Another object of the invention concerns the use of a postbiotic composition, as defined in the section "Engineered postbiotic" above, comprising at least one postbiotic, as defined in the section "Engineered postbiotic" above, and at least one bacteriocin and/or endolysin, as defined in the section "Engineered postbiotic" above, for the manufacture of a medicament intended to treat folliculitis, wherein said at least one postbiotic and at least one bacteriocin and/or endolysin have a synergistic effect in the treatment of folliculitis.

By "folliculitis" is meant a condition involving inflammation of the hair follicle, usually by a bacteria or fungus infection. Folliculitis can also be caused when hair follicles are damaged by friction from clothing, an insect bite, blockage of the follicle, shaving, or tight braids too close to the scalp.

As well-known from the skilled person, folliculitis is often due to inflammation of the hair follicle by *Staphylococcus aureus*.

Accordingly, in said embodiment, said at least one bacteriocin and/or endolysin preferably targets, in particular specifically targets, *Staphylococcus aureus*. Examples of bacteriocins targeting *S. aureus* are well-known from the skilled person and typically include Aureocins A70, A53 and 215FN, Pep5, Epidermin K7, Epicidin 280, Morricin 269, Kurstacin 287, Kenyacin 404, Entomocin 420, Tolworthcin 524, Lysostaphin, Epidermicin NI01, Pediocina PA-1, Nisin A, lacticin Q, Nukacin ISK-1, Lacticin 3147, Enterocin CCM 4231, E 50-52, OR-70 II, Duracin 61A, Reuterin, and Pentocin JL-1. Examples of endolysins targeting *S. aureus* are well-known from the skilled person and typically include $CHAP_K$, ClyS, λ SA2-E-Lyso-SH3b, λ SA2-E-LysK-SH3b, PlyGRCS, LysH5, and SAL-2.

In a particular embodiment, said at least one bacteriocin and/or endolysin is lysostaphin.

In a particular embodiment, said postbiotic composition further stimulates growth of commensal skin bacterial species such as *S. epidermidis*.

In a more preferred embodiment, said at least one bacteriocin and/or endolysin preferably targets, in particular specifically targets, *Staphylococcus aureus*, and said postbiotic further stimulates growth of commensal skin bacterial species such as *S. epidermidis*. Such a synergistic effect is particularly useful because, without being bound by theory, it is believed that it enables killing *S. aureus* bacteria which are responsible for the folliculitis onset, and making the niche, left empty by the killed *S. aureus* bacteria, be colonized by commensal skin bacterial species, in particular by *S. epidermidis*. Moreover, by decreasing inflammation, the postbiotic typically leads to a faster return to homeostasis.

In another particular embodiment, the postbiotic composition, as defined in the section "Engineered postbiotic" above, comprising at least one postbiotic, as defined in the section "Engineered postbiotic" above and at least one bacteriocin and/or endolysin, as defined in the section "Engineered postbiotic" above, is for use for treating, in a subject, a disease selected from the group consisting of impetigo, ecthyma, cellulitis, furunculosis, carbunculosis, paronychia, atopic dermatitis and botryomycosis.

The present invention further concerns a method for treating a disease selected from the group consisting of impetigo, ecthyma, cellulitis, furunculosis, carbunculosis, paronychia and botryomycosis, in a subject in need thereof, comprising administering, to said subject in need thereof, a therapeutically effective amount of a postbiotic composition, as defined in the section "Engineered postbiotic" above, comprising at least one postbiotic, as defined in the section "Engineered postbiotic" above and at least one bacteriocin and/or endolysin, as defined in the section "Engineered postbiotic" above, wherein said at least one postbiotic and said at least one bacteriocin and/or endolysin have a synergistic disease in the treatment of said disease in said subject.

Another object of the invention concerns the use of a postbiotic composition, as defined in the section "Engineered postbiotic" above, comprising at least one postbiotic, as defined in the section "Engineered postbiotic" above and at least one bacteriocin and/or endolysin, as defined in the section "Engineered postbiotic" above, for the manufacture of a medicament intended to treat a disease selected from the group consisting of impetigo, ecthyma, cellulitis, furunculosis, carbunculosis, paronychia and botryomycosis, wherein said at least one postbiotic and said at least one bacteriocin and/or endolysin have a synergistic disease in the treatment of said disease.

By "impetigo" is meant herein a bacterial infection that involves the superficial skin, and which most common presentation is yellowish crusts on the face, arms, or legs.

By "ecthyma" is meant herein a skin infection characterized by crusted sores beneath which ulcers form.

By "cellulitis" is meant herein a bacterial infection involving the inner layers of the skin, which specifically affects the dermis and subcutaneous fat, and which signs and symptoms include an area of redness which increases in size over a few days.

By "furunculosis" or "boil" is meant herein a deep folliculitis, infection of the hair follicle.

By "carbunculosis" is meant herein a condition marked by having multiple carbuncles, which are clusters of boils caused by bacterial infection.

By "paronychia" is meant herein an inflammation of the skin around the nail, which can occur suddenly or gradually.

By "botryomycosis" is meant herein a rare chronic bacterial granulomatous disease that usually involves skin and rarely viscera.

As well known from the skilled person, impetigo, ecthyma, cellulitis, furunculosis, carbunculosis, paronychia and botryomycosis are often due to *Staphylococcus aureus*. Accordingly, in said embodiment, said at least one bacteriocin and/or endolysin preferably targets, in particular specifically targets, *Staphylococcus aureus*, as defined above.

In a particular embodiment, said at least one bacteriocin and/or endolysin is lysostaphin.

In a particular embodiment, said postbiotic composition further stimulates growth of commensal skin bacterial species such as *S. epidermidis*.

In a more preferred embodiment, said at least one bacteriocin and/or endolysin preferably targets, in particular specifically targets, *Staphylococcus aureus*, and said postbiotic further stimulates growth of commensal skin bacterial species such as *S. epidermidis*. Such a synergistic effect is particularly useful because, without being bound by theory, it is believed that it enables killing *S. aureus* bacteria which are responsible for the impetigo, ecthyma, cellulitis, furunculosis, carbunculosis, paronychia or botryomycosis onset, and making the niche, left empty by the killed *S. aureus* bacteria, be colonized by commensal skin bacterial species, in particular by *S. epidermidis*.

In another embodiment, the postbiotic composition, as defined in the section "Engineered postbiotic" above, comprising at least one postbiotic, as defined in the section "Engineered postbiotic" above, and at least one bacteriocin and/or endolysin, as defined in the section "Engineered postbiotic" above, is for use for treating acne in a subject.

The present invention further concerns a method for treating acne in a subject in need thereof, comprising administering, to said subject in need thereof, a therapeutically effective amount of a postbiotic composition, as defined in the section "Engineered postbiotic" above, comprising at least one postbiotic, as defined in the section "Engineered postbiotic" above, and at least one bacteriocin and/or endolysin, as defined in the section "Engineered postbiotic" above, wherein said at least one postbiotic and said at least one bacteriocin and/or endolysin have a synergistic effect in the treatment of acne in the subject.

Another object of the invention concerns the use of a postbiotic composition, as defined in the section "Engineered postbiotic" above, comprising at least one postbiotic, as defined in the section "Engineered postbiotic" above, and at least one bacteriocin and/or endolysin, as defined in the section "Engineered postbiotic" above, for the manufacture of a medicament intended to treat acne, wherein said at least one postbiotic and said at least one bacteriocin and/or lysostaphin have a synergistic effect in the treatment of acne.

By "acne" is meant herein a skin condition arising from the pilosebaceous unit characterized by hyperkeratinization, *C. acnes* infection, and abnormal sebum production and that results in a visible skin lesion.

As well known from the skilled person, acne is often due to *Staphylococcus aureus* and *Cutibacterium acnes*, and further optionally other bacteria of the *Corynebacterium* genera. Accordingly, in said embodiment, said engineered postbiotic preferably comprises a combination of bacteriocins and/or endolysins targeting *Staphylococcus aureus*, *Cutibacterium acnes* and optionally another bacteria of the *Corynebacterium* genera.

In a particular embodiment, said engineered postbiotic comprises at least one endolysin targeting *C. acnes*, in particular at least one *C. acnes* phage endolysin targeting *C. acnes*, and at least one bacteriocin targeting *Staphylococcus* bacteria, in particular targeting *S. aureus* and/or *S. epidermidis*, more particularly at least one *Staphylococcus* bacteriocin targeting *Staphylococcus* bacteria, more particularly targeting *S. aureus* and/or *S. epidermidis*.

In a particular embodiment, said engineered postbiotic comprises at least one endolysin targeting *C. acnes*, in particular at least one *C. acnes* phage endolysin targeting *C. acnes*, and at least one endolysin targeting *Staphylococcus* bacteria, in particular at least one *Staphylococcus* phage endolysin targeting *Staphylococcus* bacteria, more particularly targeting *S. aureus* and/or *S. epidermidis*.

In a particular embodiment, said engineered postbiotic comprises at least one bacteriocin targeting *C. acnes*, and at least one bacteriocin targeting *Staphylococcus* bacteria, in particular targeting *S. aureus* and/or *S. epidermidis*, more particularly at least one *Staphylococcus* bacteriocin targeting *Staphylococcus* bacteria, more particularly targeting *S. aureus* and/or *S. epidermidis*.

In a particular embodiment, said engineered postbiotic comprises at least one bacteriocin targeting *C. acnes* and at least one endolysin targeting *Staphylococcus* bacteria, in particular at least one *Staphylococcus* phage endolysin targeting *Staphylococcus* bacteria, more particularly targeting *S. aureus* and/or *S. epidermidis*.

In a particular embodiment, said engineered postbiotic comprises (i) at least one endolysin targeting *C. acnes*, in particular at least one *C. acnes* phage endolysin targeting *C. acnes*, or at least one bacteriocin targeting *C. acnes*, and (ii) at least one endolysin targeting *Streptococcus agalactiae* or at least one bacteriocin targeting *S. agalactiae*.

In a particular embodiment, said engineered postbiotic comprises (i) at least one endolysin targeting *C. acnes*, in particular at least one *C. acnes* phage endolysin targeting *C. acnes*, or at least one bacteriocin targeting *C. acnes*, and (ii) at least one endolysin targeting *Klebsiella pneumoniae* or at least one bacteriocin targeting *K. pneumoniae*.

In a particular embodiment, said engineered postbiotic comprises (i) at least one bacteriocin targeting *Staphylococcus* bacteria, in particular targeting *S. aureus* and/or *S. epidermidis*, more particularly at least one *Staphylococcus* bacteriocin targeting *Staphylococcus* bacteria, more particularly targeting *S. aureus* and/or *S. epidermidis* or at least one endolysin targeting *Staphylococcus* bacteria, in particular at least one *Staphylococcus* phage endolysin targeting *Staphylococcus* bacteria, more particularly targeting *S. aureus* and/or *S. epidermidis*, and (ii) at least one endolysin targeting *Streptococcus agalactiae* or at least one bacteriocin targeting *S. agalactiae*.

In a particular embodiment, said engineered postbiotic comprises (i) at least one bacteriocin targeting *Staphylococcus* bacteria, in particular targeting *S. aureus* and/or *S. epidermidis*, more particularly at least one *Staphylococcus* bacteriocin targeting *Staphylococcus* bacteria, more particularly targeting *S. aureus* and/or *S. epidermidis* or at least one endolysin targeting *Staphylococcus* bacteria, in particular at least one *Staphylococcus* phage endolysin targeting *Staphylococcus* bacteria, more particularly targeting *S. aureus* and/or *S. epidermidis*, and (ii) at least one endolysin targeting *Klebsiella pneumoniae* or at least one bacteriocin target *K. pneumoniae*.

In a particular embodiment, said engineered postbiotic comprises (i) at least one endolysin targeting *C. acnes*, in particular at least one *C. acnes* phage endolysin targeting *C. acnes*, or at least one bacteriocin targeting *C. acnes*, (ii) at least one bacteriocin targeting *Staphylococcus* bacteria, in particular targeting *S. aureus* and/or *S. epidermidis*, more particularly at least one *Staphylococcus* bacteriocin targeting *Staphylococcus* bacteria, more particularly targeting *S. aureus* and/or *S. epidermidis* or at least one endolysin targeting *Staphylococcus* bacteria, in particular at least one *Staphylococcus* phage endolysin targeting *Staphylococcus* bacteria, more particularly targeting *S. aureus* and/or *S. epidermidis*, and (iii) at least one endolysin targeting *Streptococcus agalactiae* or at least one bacteriocin targeting *S. agalactiae*.

In a particular embodiment, said engineered postbiotic comprises (i) at least one endolysin targeting *C. acnes*, in particular at least one *C. acnes* phage endolysin targeting *C. acnes*, or at least one bacteriocin targeting *C. acnes*, (ii) at least one bacteriocin targeting *Staphylococcus* bacteria, in particular targeting *S. aureus* and/or *S. epidermidis*, more particularly at least one *Staphylococcus* bacteriocin targeting *Staphylococcus* bacteria, more particularly targeting *S. aureus* and/or *S. epidermidis* or at least one endolysin targeting *Staphylococcus* bacteria, in particular at least one *Staphylococcus* phage endolysin targeting *Staphylococcus* bacteria, more particularly targeting *S. aureus* and/or *S. epidermidis*, and (iii) at least one endolysin targeting *Klebsiella pneumoniae* or at least one bacteriocin target *K. pneumoniae*.

In a particular embodiment, said engineered postbiotic comprises (i) at least one endolysin targeting *C. acnes*, in particular at least one *C. acnes* phage endolysin targeting *C. acnes*, or at least one bacteriocin targeting *C. acnes*, (ii) at least one bacteriocin targeting *Staphylococcus* bacteria, in particular targeting *S. aureus* and/or *S. epidermidis*, more particularly at least one *Staphylococcus* bacteriocin targeting *Staphylococcus* bacteria, more particularly targeting *S. aureus* and/or *S. epidermidis* or at least one endolysin targeting *Staphylococcus* bacteria, in particular at least one *Staphylococcus* phage endolysin targeting *Staphylococcus* bacteria, more particularly targeting *S. aureus* and/or *S. epidermidis*, (iii) at least one endolysin targeting *Streptococcus agalactiae* or at least one bacteriocin targeting *S. agalactiae*, and (iv) at least one endolysin targeting *Klebsiella pneumoniae* or at least one bacteriocin target *K. pneumoniae*.

In a particular embodiment, said at least one endolysin targeting *C. acnes*, in particular at least one *C. acnes* phage endolysin targeting *C. acnes*, does not target *Propionibacterium granulosum, Propionibacterium humerusii* and/or *Propionibacterium avidum*. In a more particular embodiment, said at least one endolysin targeting *C. acnes*, in particular at least one *C. acnes* phage endolysin targeting *C. acnes*, is modified to not target *Propionibacterium granulosum, Propionibacterium humerusii* and/or *Propionibacterium avidum*.

Examples of bacteriocins targeting *Cutibacterium acnes* are well-known from the skilled person and typically include Lacticin 3147, Epidermin and Gallidermin. Examples of endolysins targeting *C. acnes* are well-known from the skilled person and typically include Gp20 and lysB.

Examples of bacteriocins targeting *S. aureus* are well-known from the skilled person and typically include Aureocins A70, A53 and 215FN, Pep5, Epidermin K7, Epicidin 280, Morricin 269, Kurstacin 287, Kenyacin 404, Entomocin 420, Tolworthcin 524, Lysostaphin, Epidermicin NI01, Pediocina PA-1, Nisin A, lacticin Q, Nukacin ISK-1, Lacticin 3147, Enterocin CCM 4231, E 50-52, OR-70 II, Duracin 61A, Reuterin, and Pentocin JL-1. Examples of endolysins targeting *S. aureus* are well-known from the skilled person and typically include CHAPK, ClyS, λ SA2-E-Lyso-SH3b, λ SA2-E-LysK-SH3b, PlyGRCS, LysH5, and SAL-2.

In a particular embodiment, said at least one bacteriocin targeting *S. aureus* is Lysostaphin.

Examples of bacteriocins targeting *S. epidermidis* are well-known from the skilled person and typically include A53, Pep5, Epidermin, Epilancin, Epicidin and A70. Examples of endolysins targeting *S. epidermidis* are well-known from the skilled person and typically include LysH5, LysSA12 and Lys109.

Examples of bacteriocins targeting *Streptococcus agalactiae* are well-known from the skilled person and typically include Epidermin, Aureocins A45 and A70, Pep5.

Examples of endolysins targeting *S. agalactiae* are well-known from the skilled person and typically include PlySK1249.

Examples of bacteriocins targeting *Klebsiella pneumoniae* are well-known from the skilled person and typically include klebicins. Examples of endolysins targeting *K. pneumoniae* are well-known from the skilled person and typically include ElyA1, Abtn-4, LysPA26.

In a particular embodiment, said postbiotic composition further stimulates growth of commensal skin bacterial species such as *S. epidermidis*.

In a more preferred embodiment, said at least one bacteriocin and/or endolysin preferably targets *Staphylococcus aureus, Cutibacterium acnes* and optionally another bacteria of the *Corynebacterium* genera, and said postbiotic further stimulates growth of commensal skin bacterial species such as *S. epidermidis*. Such a synergistic effect is particularly useful because, without being bound by theory, it is believed that it enables killing *Staphylococcus aureus* bacteria, *Cutibacterium acnes* bacteria, and optionally another bacteria of the *Corynebacterium* genera which are responsible for acne onset, and making the niche, left empty by the killed bacteria, be colonized by commensal skin bacterial species, in particular by *S. epidermidis*.

In another embodiment, the postbiotic composition, as defined in the section "Engineered postbiotic" above, comprising at least one postbiotic, as defined in the section "Engineered postbiotic" above and at least one bacteriocin and/or endolysin, as defined in the section "Engineered postbiotic" above, is for use for treating a bacterial infection in a subject, in particular a skin bacterial infection.

The present invention further concerns a method for treating a bacterial infection in a subject in need thereof, in particular a skin bacterial infection, comprising administering, to said subject in need thereof, a therapeutically effective amount of a postbiotic composition, as defined in the section "Engineered postbiotic" above, comprising at least one postbiotic, as defined in the section "Engineered postbiotic" above and at least one bacteriocin and/or endolysin, as defined in the section "Engineered postbiotic" above, wherein said postbiotic and said at least one bacteriocin and/or lysostaphin have a synergistic effect in the treatment of the bacterial infection in the subject.

Another object of the invention concerns the use of a postbiotic composition, as defined in the section "Engineered postbiotic" above, comprising at least one postbiotic, as defined in the section "Engineered postbiotic" above, and at least one bacteriocin and/or endolysin, as defined in the section "Engineered postbiotic" above, for the manufacture of a medicament intended to treat a bacterial infection in a subject, in particular a skin bacterial infection, wherein said at least one postbiotic and said at least one bacteriocin and/or endolysin have a synergistic effect in the treatment of the bacterial infection in the subject.

Examples of skin bacterial infection are well-known from the skilled person, and typically include impetigo (typically to *S. pyogenes*), ecthyma (typically due to *S. pyogenes*), erysipelas (typically due to *S. pyogenes*), necrotizing fasciitis (typically due to *S. pyogenes*), blistering distal dactylitis (typically due to *S. pyogenes*), erythrasma (typically due to *C. minutissimum*), erysipeloid (typically due to *Erysipelothrix rhusiopathiae*), anthrax (typically due to *B. anthracis*), cellulitis (typically due to *Helicobacter cinaedi*), ecthyma gangrenosum (typically to *P. aeruginosa*), toe web infections (typically due to *P. aeruginosa*), green nail syndrome (typically due to *P. aeruginosa*), septic arthritis (typically due to *Pasteurella multocida*), cat scratch disease (typically due to *Bartonella henselae*), bacillary angiomatosis (typically due to *Bartonella henselae* or *B. quintana*), trench fever (typically due to *B. quintana*), verruga peruana (typically due to *B. bacilliformis*), Oroya fever (typically due to *B. bacilliformis*), rhinoscleroma (typically due to *Klebsiella rhinoscleromatis*).

In said embodiment, said at least one bacteriocin and/or endolysin preferably targets, in particular specifically targets, the bacterial species which is the cause of said infection, as disclosed above.

In a particular embodiment, said postbiotic composition further stimulates growth of commensal skin bacterial species.

In a more preferred embodiment, said at least one bacteriocin and/or endolysin preferably targets the bacterial species which is the cause of said infection, as disclosed above, and said postbiotic further stimulates growth of commensal skin bacterial species. Such a synergistic effect is particularly useful because, without being bound by theory, it is believed that it enables killing the bacterial species which is the cause of said infection, as disclosed above, and making the niche, left empty by the killed bacteria, be colonized by commensal skin bacterial species.

In another embodiment, the postbiotic composition, as defined in the section "Engineered postbiotic" above, comprising at least one postbiotic, as defined in the section "Engineered postbiotic" above, and at least one bacteriocin and/or endolysin, as defined in the section "Engineered postbiotic" above, is for use for treating, in a subject, a disease or disorder associated with dysbiosis in said subject, in particular associated with skin and/or mucosa dysbiosis.

The present invention further concerns a method for treating in a subject in need thereof, a disease or disorder associated with dysbiosis in said subject, in particular associated with skin and/or mucosa dysbiosis, comprising administering, to said subject in need thereof, a therapeutically effective amount of a postbiotic composition, as defined in the section "Engineered postbiotic" above, comprising at least one postbiotic, as defined in the section "Engineered postbiotic" above, and at least one bacteriocin and/or endolysin, as defined in the section "Engineered postbiotic" above, wherein said at least one postbiotic and said at least one bacteriocin and/or endolysin have a synergistic effect in the treatment of said disease or disorder in said subject.

Another object of the invention concerns the use of a postbiotic composition, as defined in the section "Engineered postbiotic" above, comprising at least one postbiotic, as defined in the section "Engineered postbiotic" above, and at least one bacteriocin and/or endolysin, as defined in the section "Engineered postbiotic" above, for the manufacture of a medicament intended to treat in a subject, a disease or disorder associated with dysbiosis in said subject, in particular associated with skin and/or mucosa dysbiosis, wherein said at least one postbiotic and said at least one bacteriocin and/or endolysin have a synergistic effect in the treatment of said disease or disorder in said subject.

By "dysbiosis" is meant herein, a microbial imbalance or maladaptation on or inside the body.

Examples of diseases or disorders associated with dysbiosis are well-known from the skilled person and typically include atopic dermatitis, psoriasis, progressive macular hypomelanosis (PMH) and seborrheic dermatitis.

In said embodiment, said at least one bacteriocin and/or endolysin preferably targets, in particular specifically targets, the bacterial species which are the cause of the dysbiosis, such as bacterial species which are over-represented compared to a healthy microbiota.

In a particular embodiment, said postbiotic composition further stimulates growth of commensal skin bacterial species, in particular bacterial species which are under-represented compared to a healthy microbiota.

In a more preferred embodiment, said at least one bacteriocin and/or endolysin preferably targets which are the cause of the dysbiosis, such as bacterial species which are over-represented compared to a healthy microbiota, and said postbiotic further stimulates growth of commensal skin bacterial species, in particular bacterial species which are under-represented compared to a healthy microbiota. Such a synergistic effect is particularly useful because, without being bound by theory, it is believed that it enables killing which are the cause of the dysbiosis, such as bacterial species which are over-represented compared to a healthy microbiota, and making the niche, left empty by the killed bacteria, be colonized by commensal skin bacterial species, in particular bacterial species which are under-represented compared to a healthy microbiota.

In a particular embodiment, the postbiotic composition, as defined in the section "Engineered postbiotic" above, comprising at least one postbiotic, as defined in the section "Engineered postbiotic" above, and at least one bacteriocin and/or endolysin, as defined in the section "Engineered postbiotic" above, is for use for treating atopic dermatitis in a subject.

The present invention further concerns a method for treating atopic dermatitis in a subject in need thereof, comprising administering, to said subject in need thereof, a therapeutically effective amount of a postbiotic composition, as defined in the section "Engineered postbiotic" above, comprising at least one postbiotic, as defined in the section "Engineered postbiotic" above, and at least one bacteriocin and/or endolysin, as defined in the section "Engineered postbiotic" above, wherein said at least one postbiotic and said at least one bacteriocin and/or endolysin have a synergistic effect in the treatment of atopic dermatitis in said subject.

Another object of the invention concerns the use of a postbiotic composition, as defined in the section "Engineered postbiotic" above, comprising at least one postbiotic, as defined in the section "Engineered postbiotic" above, and at least one bacteriocin and/or endolysin, as defined in the section "Engineered postbiotic" above, for the manufacture of a medicament intended to treat atopic dermatitis in a subject, wherein said at least one postbiotic and said at least one bacteriocin and/or endolysin have a synergistic effect in the treatment of atopic dermatitis in said subject.

By "atopic dermatitis" or "atopic eczema" is meant herein a long-term type of inflammation of the skin (dermatitis) which results in itchy, red, swollen, and cracked skin.

As reminded in Lin et al. (2007) *Clinic Rev. Allerg. Immunol.* 33:167-177, the skin of subjects suffering from atopic dermatitis is more likely to be colonized and infected with *S. aureus*. When on atopic dermatitis skin, *S. aureus* can secrete various exotoxins acting as superantigens, which penetrate the skin barrier and contribute to the persistence and exacerbation of skin inflammation in atopic dermatitis.

Accordingly, in said embodiment, said at least one bacteriocin and/or endolysin preferably targets, in particular specifically targets, *Staphylococcus aureus*. Examples of bacteriocins targeting *S. aureus* are well-known from the skilled person and typically include Aureocins A70, A53 and 215FN, Pep5, Epidermin K7, Epicidin 280, Morricin 269, Kurstacin 287, Kenyacin 404, Entomocin 420, Tolworthcin 524, Lysostaphin, Epidermicin NI01, Pediocina PA-1, Nisin A, lacticin Q, Nukacin ISK-1, Lacticin 3147, Enterocin CCM 4231, E 50-52, OR-70 II, Duracin 61A, Reuterin, and Pentocin JL-1. Examples of endolysins targeting *S. aureus* are well-known from the skilled person and typically include CHAP$_K$, ClyS, λ SA2-E-Lyso-SH3b, λ SA2-E-LysK-SH3b, PlyGRCS, LysH5, and SAL-2.

In a particular embodiment, said at least one bacteriocin and/or endolysin is lysostaphin.

In a particular embodiment, said postbiotic composition further stimulates growth of commensal skin bacterial species such as *S. epidermidis*.

In a more preferred embodiment, said at least one bacteriocin and/or endolysin preferably targets, in particular specifically targets, *Staphylococcus aureus*, and said postbiotic further stimulates growth of commensal skin bacterial species such as *S. epidermidis*. Such a synergistic effect is particularly useful because, without being bound by theory, it is believed that it enables killing *S. aureus* bacteria which contribute to the persistence and exacerbation of skin inflammation in atopic dermatitis, and making the niche, left empty by the killed *S. aureus* bacteria, be colonized by commensal skin bacterial species, in particular by *S. epidermidis*. Moreover, by decreasing inflammation, the postbiotic typically leads to a faster return to homeostasis.

In another embodiment, the postbiotic composition, as defined in the section "Engineered postbiotic" above, comprising at least one postbiotic, as defined in the section "Engineered postbiotic" above, and at least one bacteriocin and/or endolysin, as defined in the section "Engineered postbiotic" above, is for use for improving wound healing.

The present invention further concerns a method for improving wound healing in a subject in need thereof, comprising administering, to said subject in need thereof, a therapeutically effective amount of a postbiotic composition, as defined in the section "Engineered postbiotic" above, comprising at least one postbiotic, as defined in the section "Engineered postbiotic" above, and at least one bacteriocin and/or endolysin, as defined in the section "Engineered postbiotic" above, wherein said at least one postbiotic and said at least one bacteriocin and/or endolysin have a synergistic effect in the improvement of wound healing in the subject.

Another object of the invention concerns the use of a postbiotic composition, as defined in the section "Engineered postbiotic" above, comprising at least one postbiotic, as defined in the section "Engineered postbiotic" above and at least one bacteriocin and/or endolysin, as defined in the section "Engineered postbiotic" above, for the manufacture of a medicament intended to improve wound healing, wherein said at least one postbiotic and said at least one bacteriocin and/or endolysin have a synergistic effect in the improvement of wound healing.

By "wound healing" is meant herein the repair or replacement of injured tissues, including the skin, muscle, nervous tissue, bone, soft tissue, internal organ and blood vessel tissue. Such wound healing results from a series of tissue responses, such as acute and chronic inflammation, cellular migration, angiogenesis and extracellular matrix (ECM) accumulation.

As demonstrated in the examples below, the postbiotic composition of the invention is able to improve wound healing, in particular to accelerate wound healing.

In a particular embodiment, the subject to be treated has been diagnosed with, or is at risk of developing a disease or disorder as defined above. Diagnostic methods of such disease or disorder are well known by the man skilled in the art.

In a particular embodiment, the disease or disorder presents a resistance to treatment, preferably the disease or disorder presents an antibiotic resistance.

In a particular embodiment, the subject has never received any treatment prior to the administration of the engineered postbiotic of the invention.

In a particular embodiment, the subject has already received at least one line of treatment, preferably several lines of treatment, prior to the administration of the engineered postbiotic of the invention.

In a particular embodiment of the therapeutic methods of the invention, said postbiotic composition is administered topically.

Alternatively, said postbiotic composition may be administered transdermally, sublingually, parenterally, gastrointestinally; transbronchially and transalveolarly. Parenteral routes of administration include but are not limited to electrical or direct injection such as direct injection into a central venous line, intravenous, intramuscular, intraperitoneal or subcutaneous injection. Gastrointestinal routes of administration include but are not limited to oral and rectal administration. Transbronchial and transalveolar routes of administration include but are not limited to inhalation, either via the mouth or intranasally.

In a particularly preferred embodiment, said postbiotic composition is in the form of a pharmaceutical formulation for topical application.

The form of the pharmaceutical compositions, the route of administration and the dose of administration of the postbiotic composition of the invention, can be adjusted by the man skilled in the art according to the type and severity of the disease or disorder (e.g. depending on the bacteria species involved in the disease, disorder and/or infection, and its localization in the patient's body), and to the patient, in particular its age, weight, sex, and general physical condition.

Particularly, the amount of postbiotic composition of the invention to be administered has to be determined by standard procedure well known by those of ordinary skills in the art. Physiological data of the patient (e.g. age, size, and weight) and the routes of administration have to be taken into account to determine the appropriate dosage, so as a therapeutically effective amount will be administered to the patient.

Preferably, the treatment is administered regularly, preferably between every day and every month, more preferably between every day and every two weeks, more preferably between every day and every week, even more preferably the treatment is administered every day.

The duration of treatment with the postbiotic composition of the invention is preferably comprised between 1 day and 20 weeks, more preferably between 1 day and 10 weeks, still more preferably between 1 day and 4 weeks, even more preferably between 1 day and 2 weeks. In a particular embodiment, the duration of the treatment is of about 1 week. Alternatively, the treatment may last as long as the disease or disorder persists.

Pharmaceutical Formulation

The present invention also relates to a formulation, in particular a pharmaceutical formulation, comprising:
(i) a postbiotic composition comprising at least one postbiotic, in particular engineered postbiotic, as defined in the section "Engineered postbiotic" above and at least one bacteriocin and/or endolysin, as defined in the section "Engineered postbiotic" above (ii) at least one pharmaceutically acceptable excipient and/or adjuvant selected from the group consisting of disintegrants, binders, bulking agents/fillers, lubricants, glidants, wetting agents, penetration/permeation enhancers, mucoadhesive agents, preservatives, antifoaming agents, suspending agents, viscosity modifying agents, coloring agents, antioxidants, and combinations thereof, and (iii) optionally an additional therapeutically active agent.

In a particular embodiment, said postbiotic, in particular engineered postbiotic, is obtained from microorganisms, in particular bacteria, heterologously expressing said at least one bacteriocin and/or endolysin, as defined in the section "Engineered postbiotic" above. In a particular embodiment, said postbiotic, in particular engineered postbiotic, comprises at least one microbial, in particular bacterial, lysate, as defined in the section "Engineered postbiotic" above, preferably obtained from microorganisms, in particular bacteria, heterologously expressing said at least one bacteriocin and/or endolysin, as defined in the section "Engineered postbiotic" above.

In a particular embodiment, said postbiotic is obtained from *L. rhamnosus* bacteria, in particular *L. rhamnosus* GG bacteria, heterologously expressing said at least one bacteriocin and/or endolysin, as defined in the section "Engineered postbiotic" above, more particularly expressing lysostaphin. In a particular embodiment, said postbiotic, in particular engineered postbiotic, comprises at least one bacterial lysate obtained from *L. rhamnosus* bacteria, in particular *L. rhamnosus* GG bacteria, heterologously expressing said at least one bacteriocin and/or endolysin, as defined in the section "Engineered postbiotic" above, more particularly expressing lysostaphin.

By "pharmaceutical formulation" is meant herein a composition intended to procure a therapeutic effect.

By "pharmaceutically acceptable excipient" is meant herein a non-pharmaceutically active additive used in the manufacture of a pharmaceutical composition, which allows the pharmaceutically active ingredient to be manufactured into a pharmaceutical formulation or a galenic formulation providing the necessary bioavailability of the medicament to the patient upon the administration of the pharmaceutical composition. The excipient is preferably compatible with the other ingredients of the composition and produces no adverse effect, allergic reaction or other undesirable reaction when it is administered to a human or an animal.

By "pharmaceutically acceptable adjuvant" is meant herein a substance that is non-toxic, biologically tolerable, and otherwise biologically suitable for administration to a subject, added to a pharmaceutical composition to strengthen the role of the excipient or of a therapeutically active ingredient.

By "disintegrant" is meant herein an excipient which can take up water and swell and thus improve disintegration of a tablet or granules. Examples of disintegrants include croscarmellose sodium; starch (paste and pre-gelatinized), such as sodium starch glycolate, sodium salt of carboxymethyl starch; methacrylic acid polymer with divinylbenzene, potassium salt, Maltodextrin; crospovidone.

By "binder" is meant herein an excipient holding the ingredients of a formulation together. Examples of binders include povidone, pregelatinized starch, dextrin, gelatin, hydroxypropyl methylcellulose, maltodextrin, starch, zein, acacia, alginic acid, carbomers (cross-linked polyacrylates), polyacrylamide, polymethacrylates, carboxymethylcellulose sodium, ethylcellulose, guar gum, cellulose gum, xanthan gum, hydrogenated vegetable oil (type 1), hydroxyethyl cellulose, hydroxypropyl cellulose, methylcellulose, magnesium aluminum silicate, and/or sodium alginate.

By "bulking agent" or "filler" is meant herein an excipient used to increase the volume of the material to enable easier processing of the ingredients and make it into a size suitable for consumption. Non-limiting examples of fillers include carbohydrates, inorganic compounds, and polyvinylpirrolydone. Other non-limiting examples of fillers include dibasic calcium sulfate, tribasic calcium sulfate, starch, calcium carbonate, magnesium carbonate, microcrystalline cellulose, dibasic calcium phosphate, tribasic calcium phosphate, magnesium carbonate, magnesium oxide, calcium silicate, talc, modified starches, lactose, sucrose, mannitol, and sorbitol.

By "lubricant" is meant herein an excipient used to reduce friction. Examples of lubricant include but not limited to calcium stearate, magnesium stearate, polyethylene glycol, sodium benzoate, potassium benzoate, sodium lauryl sulfate, talc, stearic acid, zinc stearate or mixture thereof.

By "glidant" is meant herein an excipient added to a powder to improve its flowability. Examples of glidant include but not limited to talc, colloidal silicon dioxide, starch, magnesium stearate or mixture thereof.

By "wetting agent" is meant herein an excipient which allows dispersion of particles in a medium. Examples of wetting agent include, but are not limited to, compounds selected from the group consisting of: glycerol (glycerin), propylene glycol, sorbitol, trehalose, triacetin, cyclomethicone, and mixtures thereof.

As used herein, "penetration enhancer" and "permeation enhancer" refer to any compound that enhances the penetration of compositions of the present invention and/or permeation of barriers such as the skin and cell walls. Some examples of penetration/permeation enhancers that may be used in the present invention include pyrrolidones, for example 2-pyrrolidone; alcohols, such as ethanol; alkanols, such as decanol; glycols, such as propylene glycol, dipropylene glycol, butylenes glycol; surfactants; glycerol derivatives, or terpenes.

As used herein, "mucoadhesive agents" refers to excipients which exhibit an affinity for a mucosa surface. Examples of mucoadhesive agents typically include, but are not limited to, pectin, alginic acid, chitosan, hyaluronic acid, polysorbates, such as polysorbate-20, -21, -40, -60, -61, -65, -80, -81, -85; poly(ethylene glycol), such as PEG-7, -14, -16, -18, -55, -90, -100, -135, -180, -4, -240, -6, -8, -9, -10, -12, -20, or -32; oligosaccharides and polysaccharides, such as gellan, carrageenan, xanthan gum, gum arabic, and dextran; cellulose esters and cellulose ethers; modified cellulose polymers, such as carboxymethylcellulose, hydroxyethylcellulose, hydroxypropyl methylcellulose, hydroxyethyl ethylcellulose; polyether polymers and oligomers, such as polyoxyethylene; condensation products of poly(ethylene oxide) with various reactive hydrogen containing compounds having long hydrophobic chains, condensation products of poly(ethylene oxide) with fatty acids, fatty alcohols, fatty amides, polyhydric alcohols; polyether compounds, such as poly(methyl vinyl ether), polyoxypropylene of less than 10 repeating units; polyether compounds, such as block copolymers of ethylene oxide and propylene oxide.

As used herein, a "preservative agent" is an excipient that controls the microbial bioburden of the formulation. Examples of preservative agent include but are not limited to, compounds selected from the group consisting of: phenylpropanol, bronopol, butylparaben, ethylparaben, imidazolidinyl urea, methylparaben, phenoxyethanol, sodium benzoate, potassium sorbate and mixtures thereof.

As used herein, an "anti-foaming agent" refers to an excipient that reduces and hinders the formation of foam in pharmaceutical processes or bioprocesses. Examples of anti-foaming agents include insoluble oils, dimethyl polysiloxanes (Simethicone emulsion) and other silicones, certain alcohols, stearates and glycols.

The term "suspending agent" as used herein refers to a pharmaceutical acceptable excipient that promotes particle suspension or dispersion and reduces sedimentation. Examples of suspending agents include polysaccharides, inorganic salts, and polymers. Specific examples of suspending agents include, without limitation, alginates, methylcellulose, hydroxyethylcellulose, carboxymethylcellulose, colloidal silicon dioxide, agar, calcium stearate, hypromellose, magnesium aluminum silicate, guar gum, carboxymethylcellulose sodium, microcrystalline cellulose, acacia, tragacanth, xanthan gum, bentonite, carbomer, carrageenan, powdered cellulose, gelatin, polyethylene glycol, povidone, dextrin, medium-chain triglycerides, sucrose, hydroxypropyl methyl cellulose, chitosan, polyoxyethylene, polyoxypropylene ethers and combinations thereof.

As used herein, "viscosity modifying agents" refer to excipients that change the thickness or texture of pharmaceutical ingredients. Viscosity modifiers can include such products as thickeners, texturizers, gelation agents and stiffening agents. Examples of viscosity modifying agents include hydroxypropylcellulose, methylcellulose, hydroxyethylcellulose, hydroxypropylmethyl cellulose, hydroxyethylpropyl cellulose, polyethylene glycol, propylene glycol, starches, such as maize or corn starch, potato starch, rice starch, tapioca starch and wheat starch, hydroxypropyl starch, carboxyvinyl polymers, carbomers such as Carbopol, carboxymethyl cellulose and salts thereof, microcrystalline cellulose, agar, polyvinyl alcohol, alginic acid, potassium alginate, polyvinyl pyrrolidone, carmellose sodium, maltodextrin, dextrin, gelatin, pectin, poloxamer, polycarbophil, pregelatinized starch, polysaccharide gums such as guar, acacia, gellan, carrageenan, xanthan and tragacanth gums and mixtures of two or more thereof.

By "coloring agents" is meant herein colorants mainly used to impart a distinctive appearance to the pharmaceutical dosage forms. Examples of coloring agents include beta-carotene, indigo carmine, Sunset Yellow FCF, tartrazine, Brilliant Blue FCF, titanium dioxide, Quinoline Yellow SS, Allura Red AC, Quinizarine Green SS and iron oxides.

By "antioxidant" is meant herein an excipient added to enhance physical and chemical stability of the formulation. Examples of antioxidants include, but are not limited to anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxanthin, alpha-carotene, beta-carotene, beta-apo-carotenoic acid, carnosol, carvacrol, catechins, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, edetic acid, ellagic acid, erythorbic acid, sodium erythorbate, escuietin, esculin, 6-ethoxy-1,2-dihydro-2,2,4-trimethylquinoline, ethyl maltol, ethylenediaminetetraacetic acid (EDTA) and EDTA salts, eucalyptus extract, eugenol, ferulic acid, flavonoids (e.g., catechin, epicatechin, epigallocatechin (EGC)), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinnamic acid, hydroxyglutaric acid, hydroquinone, N-hydroxysuccinic acid, hydroxytyrosol, hydroxyurea, rice bran extract, lactic acid and its salts, lecithin, lecithin citrate; R-alpha-lipoic acid, lutein, lycopene, malic acid, maltol, 5-methoxy tryptamine, monoglyceride citrate; mono isopropyl citrate; morin, beta-naphthoflavone, nordihydroguaiaretic acid (NDGA), oxalic acid, palmityl citrate, phenothiazine, phosphatidylcholine, phosphoric acid, phosphates, phytic acid, phytyl ubichromel, pimento extract, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosoS, vanillic acid, 2,6-di-tert-butyS-4-hydroxymethylphenol (i.e., Ionox 100), 2,4-(tris-3'[5'-bi-tert-butyl-4'-hydroxybenzyl)-mesitylene (i.e., Ionox 330), 2,4,5-trihydroxy butyrophenone, ubiquinone, tertiary butyl hydroquinone (TBHQ), thiodipropionic acid, trihydroxy butyrophenone, tryptamine, tyramine, uric acid, vitamin K and derivatives, vitamin Q10, wheat germ oil, zeaxanthin, or combinations thereof.

In a particular embodiment, said formulation may further comprise additional pharmaceutically acceptable excipients selected from emollients/humectants/moisturizers, surfactant/emulsifying agents, absorbents, chelating agents, denaturants, solubilizing agents, buffering agents and solvents.

Examples of emollients/humectants/moisturizers include phospholipids, ceramide, glycerin, cetyl alcohol, cetearyl isononanoate, cetearyl octanoate, decyl oleate, isooctyl stearate, coco caprylate/caprate, ethylhexyl hydroxystearate, ethylhexyl isononanoate, isoproyl palmitate, isopropyl isostearate, isopropyl myristate, oleyl oleate, hexyl laurate, paraffinum liquidum, C13-14 isoparaffin, PEG-75 lanolin, PEG-7 glyceryl cocoate, petrolatum, ozokerite, cyclomethicone, dimethicone, dimethicone copolyol, dicaprylyl ether, *Butyrospermum parkii, Buxus chinensis,* canola, *Carnauba cera, Copernicia cerifera, Oenothera biennis, Elaeis guineensis, Prunus dulcis,* squalane, *Zea mays, Glycine soja, Helianthus annuus* seed oil, lanolin, hydrogenated castor oil, hydrogenated coconut oil, avocado oil, hydrogenated polyisobutene, sucrose cocoate, stearoxy dimethicone, lanolin alcohol, isohexadecane, butylene glycol, caprylic/capric triglyceride, dimyristyl tartrate, glucose, glycereth-26, glyceryl stearate, hydrolyzed milk protein, lactic acid, lactose and other sugars, laureth-8, lecithin, octoxyglycerin, PEG-12, PEG-135, PEG-150, PEG-20, PEG-8, caprylyl glycol, pentylene glycol, hexylene glycol, phytantriol, polyquaternium-39, PPG-20 methyl glucose ether, propylene glycol, sodium hyaluronate, sodium lactate, sodium PCA (sodium salt of 1-pyrrolidone carboxylic acid), sorbitol, succinoglycan, synthetic beeswax, tri-C14 15 alkyl citrate and starch.

Examples of surfactant/emulsifying agents include ceteareths, ceteths, laneths, laureths such as laureth-7, isoseareths, steareths, cetyl alcohol, deceths, dodoxynols, glyceryl palmitate, glyceryl stearate, laneths, myreths, nonoxynols, octoxynols, oleths, PEG-castor oil, poloxamers (e.g., poloxamer 407), poloxamines, polysorbates, sodium laurate, ammonium laureth sulfate, sodium laureth sulfate, sodium lauroyl sarcosinate, sodium lauroyl taurate, sodium lauryl sulfate, sodium methyl cocoyl taurate, sodium methyl oleoyl taurate, sodium nonoxynol sulfate, sodium cetyl sulfate, sodium cetearyl sulfate, sodium cocoate, sodium cocoyl isethionate and sodium cocoyl sarcosinate.

Examples of absorbents include alumina, aluminum hydroxide, aluminum magnesium silicate, aluminum silicate, aluminum starch octenylsuccinate, bentonite, bismuth oxychloride, boron nitride, calcium carbonate, clay, cornstarch, fuller's earth, kaolin, magnesium, magnesium carbonate, magnesium hydroxide, montmorillonite, rice starch, silica, silicate, silt, sodium carbonate, talc and zeolite.

Examples of chelating agents include ethylene diaminetetraacetic acid (EDTA), sodium or potassium salts of EDTA such as EDTA disodium salt, EDTA trisodium salt and EDTA tetrasodium salt, cyclodextrin, pentasodium pentetate, phytic acid, potassium citrate, sodium gluconate and potassium gluconate.

Examples of solubilizing agents include polyethylene glycol, polyvinylpyrrolidone, dextran, or mixtures thereof.

Examples of buffering agents include sodium bicarbonate, potassium bicarbonate, magnesium hydroxide, magnesium lactate, magnesium gluconate, aluminum hydroxide, aluminum hydroxide/sodium bicarbonate co precipitate, a mixture of an amino acid and a buffer, a mixture of aluminum glycinate and a buffer, a mixture of an acid salt of an amino acid and a buffer, a mixture of an alkali salt of an amino acid and a buffer, sodium citrate, sodium tartarate, acetic acid and acetates of sodium, sodium carbonate, sodium polyphosphate, potassium polyphosphate, sodium pyrophosphate, potassium pyrophosphate, disodium hydrogen phosphate, dipotassium hydrogenphosphate, trisodium phosphate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and other calcium salts, citric acid and citrates of sodium or potassium, phosphoric acid and phosphates of sodium and of potassium.

Examples of solvents include water and aqueous solvents such as n-butanol, isopropyl alcohol, n-propanol, ethanol, 1,2-hexanediol and methanol.

In a particular embodiment, said formulation, in particular said pharmaceutical composition comprises at least one humectant, at least one bulking agent, at least one binder and at least one preservative, as defined above. In a particular embodiment, said formulation, in particular said pharmaceutical formulation, further comprises at least one emollient, at least one chelating agent, and at least one buffering agent, as defined above. In a more particular embodiment, said formulation, in particular said pharmaceutical formulation, further comprises at least one skin conditioning agent, as defined above.

By "additional therapeutically active agent" is meant herein any chemical, biochemical, organic, inorganic compound, composition, element or substance that is designated or can be used for the treatment of diseases, disorders, malfunctions, etc. of a living being or of biological material in general, and which is different from the postbiotic composition as defined in the section "Engineered postbiotic" above, in particular from the postbiotic as defined in the section "Engineered postbiotic" above and from the at least one bacteriocin and/or endolysin as defined in the section "Engineered postbiotic" above.

Said additional therapeutically active agent can be selected from the group consisting of nonsteroidal anti-inflammatory drugs (NSAIDs) analgesics; opiate agonist analgesics; salicylate analgesics; H1-blocker antihistamines; H2-blocker antihistamines; anti-infective agents; anti-anaerobic anti-infectives; antifungal antibiotic anti-infectives; macrolide antibiotic anti-infectives; miscellaneous beta-lactam antibiotic anti-infectives; penicillin antibiotic anti-infectives; quinolone antibiotic anti-infectives; tetracycline antibiotic anti-infectives; antituberculosis antimycobacterial anti-infectives; antiprotozoal anti-infectives; antimalarial antiprotozoal anti-infectives; anti-retroviral anti-infectives; antiviral anti-infective agents; alkylating antineoplastic agents; nitrosourea alkylating antineoplastic agents; antimetabolite antineoplastic agents; pyrimidine analog antimetabolite antineoplastic agents; hormonal antineoplastics; natural antineoplastics; antibiotic natural antineoplastics; vinca alkaloid natural antineoplastics; autonomic agents; anticholinergic autonomic agents; antimuscarinic anticholinergic autonomic agents; ergot alkaloid autonomic agents; cholinergic agonist parasympathomimetics; cholinesterase inhibitor parasympathomimetics; alpha-blocker sympatholytics; beta-blocker sympatholytics; adrenergic agonist sympathomimetics; cardiovascular agents; beta-blocker antianginals; calcium-channel blocker antianginals; nitrate antianginals; cardiac glycoside antiarrhythmics; class I antiarrhythmics; class II antiarrhythmics; class III antiarrhythmics; class IV antiarrhythmics; alpha-blocker antihypertensives; angiotensin-converting enzyme inhibitor (ACE inhibitor) antihypertensives; beta blocker antihypertensives; calcium-channel blocker antihypertensive agents; central-acting adrenergic antihypertensives; diuretic antihypertensive agents; peripheral vasodilator antihypertensives; antilipemics; bile acid sequestrant antilipemics; HMG-CoA reductase inhibitor antilipemics; inotropes; cardiac glycoside inotropes; thrombolytic agents or enzymes; dermatological agents; dermatological corticosteroid anti-inflammatory agents; antifungal topical antiinfectives; antiviral topical anti-infectives; topical antineoplastics; electrolytic and renal agents; loop diuretics; potassium-sparing diuretics; thiazide diuretics; uricosuric agents; enzymes such as RNase and DNase; immunosuppressive agents; antiemetics; salicylate gastrointestinal anti-inflammatory agents; gastric acid-pump inhibitor anti-ulcer agents; H2-blocker anti-ulcer agents; digestants; prokinetic agents; opiate agonist intravenous anesthetics; hematopoietic anti anemia agents; coagulation agents; anticoagulants; growth receptor inhibitors; abortifacients; antidiabetic agents; oral contraceptives; progestin contraceptives; estrogens; fertility agents; parathyroid agents; pituitary hormones; progestins; thyroid hormones; immunobiologic agents; immunoglobulins; amide local anesthetics; ester local anesthetics; musculoskeletal corticosteroid anti-inflammatory agents; musculoskeletal anti-inflammatory immunosuppressives; musculoskeletal nonsteroidal anti-inflammatory drugs (NSAIDs); skeletal muscle relaxants; reverse neuromuscular blocker skeletal muscle relaxants; neurological agents; anticonvulsants; barbiturate anticonvulsants; benzodiazepine anticonvulsants; anti-Parkinson's agents; antivertigo agents; opiate agonists; opiate antagonists; beta-blocker anti-glaucoma agents; miotic anti-glaucoma agents; ophthalmic aminoglycoside antiinfectives; ophthalmic quinolone anti-infectives; ophthalmic corticosteroid anti-inflammatory agents; ophthalmic nonsteroidal anti-inflammatory drugs (NSAIDs); antipsychotics; benzodiazepine anxiolytics, sedatives and hypnotics; psychostimulants; antitussives; bronchodilators; adrenergic agonist bronchodilators; respiratory corticosteroid anti-inflammatory agents; antidotes; heavy metal antagonists/chelating agents; deterrent substance abuse agents; withdrawal substance abuse agents; minerals, such as iron, calcium, and magnesium; vitamin B compounds, such as cyanocobalamin (vitamin B12) and niacin (vitamin B3); vitamin C compounds; vitamin D compounds, such as calcitriol; vitamin A, vitamin E, and vitamin E compounds; anti-bleeding agents; anthelmintic anti-infectives; sclerosants; anabolic agents; antacids; anti-asthmatic agents; anti-cholesterolemic and anti-lipid agents; anti-diarrheals; anti-manic agents; anti-nauseants; anti-obesity agents; antipyretic and analgesic agents; antispasmodic agents; anti-thrombotic agents; anti-uricemic agents; anti-tussives; appetite suppressants; cerebral dilators; coronary dilators; decongestants; diagnostic agents; erythropoietic agents; expectorants; gastrointestinal sedatives; hyperglycemic agents; hypoglycemic agents; ion exchange resins; laxatives; mucolytic agents; neuromuscular drugs; peripheral vasodilators; psychotropics, stimulants; thyroid and antithyroid agents; and uterine relaxants.

In a particular embodiment, said formulation may further comprise a skin care agent.

By "skin care agent" is meant herein an agent that has one or more beneficial effects on the care and/or hygiene of the skin. The skin care agent can be selected from the group consisting of antioxidants, free-radical scavengers, skin protecting agents, skin conditioning agents, skin soothing agents, and exfoliators.

By "skin conditioning agent" is meant herein an agent that can maintain the skin in a good condition. Examples of skin conditioning agents include urea, guanidine, aloe vera, glycolic acid and glycolate salts such as ammonium and quaternary alkyl ammonium, lactic acid and lactate salts such as sodium lactate, ammonium lactate and quaternary alkyl ammonium lactate, polyhydroxy alcohols such as sorbitol, glycerol, hexanetriol, tocopherol, propylene glycol, butylene glycol, hexylene glycol, polyethylene glycol, carbohydrates such as alkoxylated glucose, starches, starch derivatives, glycerin, pyrrolidone carboxylic acid (PCA), lactamide monoethanolamine, acetamide monoethanolamine, volatile silicone oils, nonvolatile silicone oils, *Helianthus annuus* seed oil, phospholipids, *Salix alba* (willow) bark extract, *Glycine soja* seed extract, and mixtures thereof.

Examples of skin soothing agents include bisabolol.

As used herein, "skin protecting agents" are agents that protect the skin against chemical irritants and/or physical irritants, such as UV light, including sunscreens, anti-wrinkle and anti-skin atrophy agents.

Examples of UV blocking agents include 2-ethylhexyl p-methoxycinnamate, 2-ethylhexyl N, N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoyl-methane, 4-isopropy dibenzoylmethane, 3-benzylidene camphor, 3-(4-methylbenzylidene) camphor, anthanilates, ultrafine titanium dioxide, zinc oxide, iron oxide, silica, 4-N, N-(2-ethylhexyl)methylaminobenzoic acid ester of 2,4-dihydroxybenzophenone, 4-N, N-(2-ethylhexyl)-methylaminobenzoic acid ester with 4-hydroxydibenzoylmethane, 4-N, N-(2-ethylhexyl)-methylaminobenzoic acid ester of 2-hydroxy-4-(2-hydroxyethoxy)benzophenone and 4-N, N(2-ethylhexyl)-methylaminobenzoic acid ester of 4-(2-hydroxyethoxy)dibenzoylmethane.

Examples of anti-wrinkle and anti-skin atrophy agents include retinoic acid and its derivatives, retinol, retinyl esters, salicylic acid and its derivatives, sulfur-containing D and L amino acids except cysteine, alpha-hydroxy acids (e.g., glycolic acid and lactic acid), phytic acid, lipoic acid and lysophosphatidic acid.

Examples of antioxidants and/or free-radical scavengers include ascorbic acid, salts of ascorbic acid such as ascorbyl palmitate and sodium ascorbate, ascorbyl glucosamine, vitamin E (i.e., tocopherols such as a-tocopherol), derivatives of vitamin E (e.g., tocopheryl acetate), retinoids such as retinoic acid, retinol, trans-retinol, cis-retinol, mixtures of trans-retinol and cis-retinol, 3-dehydroretinol and derivatives of vitamin A (e.g., retinyl acetate, retinal and retinyl palmitate, also known as tetinyl palmitate), lipoic acid, sodium citrate, sodium sulfite, lycopene, anthocyanids, bioflavinoids (e.g., hesperitin, naringen, rutin and quercetin), superoxide dismutase, glutathione peroxidase, butylated hydroxytoluene (BHT), butylated hydroxyanisole (BHA), indole-3-carbinol, pycnogenol, melatonin, sulforaphane, pregnenolone, lipoic acid and 4-hydroxy-5-methyl-3[2H]-furanone.

Examples of exfoliants include hydroxy carboxylic acids such as alpha hydroxy acids or beta hydroxy acids, keto acids and hydroxybenzoic acids.

In a particular embodiment, the formulation of the invention comprises at least 0.2% of postbiotic composition of the invention, in particular at least 0.5%, at least 1%, at least 3%, at least 5%, at least 10%, at least 15%, at least 20%, at least 30%, at least 40% or at least 50% of postbiotic composition of the invention.

In a particular embodiment, the formulation of the invention comprises between 0.2% and 20% of postbiotic composition of the invention, more particularly between 0.3% and 15% of postbiotic composition of the invention, still particularly between 0.5% and 10% of postbiotic composition of the invention, still particularly between 1% and 8% of postbiotic composition of the invention, still particularly between 3% and 5% of postbiotic composition of the invention.

The pharmaceutical formulation of the invention can be formulated under any suitable form well-known from the skilled person.

In a particular embodiment, said formulation is in the form of aqueous, hydroalcoholic or oily solutions, of dispersions in the form of solutions or dispersions of the lotion or serum type, of emulsions, in particular with liquid or semi-liquid consistency of the milk type, typically obtained by dispersion of a fatty phase in an aqueous phase (O/W) or conversely (W/O), or suspensions or emulsions of soft semi-solid or solid consistency of the cream type, of cream, of aqueous or anhydrous gel, of microemulsions, of nanoemulsions, of microcapsules, of microparticles, of ionic and/or nonionic type vesicular dispersions, of stick, of aerosol spray, of pump spray, or of foam. In a particular embodiment, said formulation is in the form of an emulsion, of a microemulsion or of a nanoemulsion.

The pharmaceutical formulation of the invention can be in any form well-known from the skilled person, typically depending on its administration route.

For oral administration, the pharmaceutical formulation can be in the form of tablets, capsules, sugar-coated pills, syrups, suspensions, solutions, powders, granules, emulsions, suspensions of microspheres or nanospheres or lipid or polymer vesicles providing controlled release.

For parenteral administration, the pharmaceutical formulation can be in the form of solutions or suspensions for infusion or for injection.

For topical application, the pharmaceutical formulation can be in the form of unguents, creams, milks, ointments, powders, impregnated tampons, solutions, gels, sprays, lotions or suspensions. It can also be in the form of suspensions of microspheres or nanospheres or lipid or polymer vesicles or polymer patches or hydrogels providing controlled release. This formulation for topical application can be in anhydrous form, in aqueous form or in the form of an emulsion.

The pharmaceutical formulation according to the present invention can be prepared by mixing the essential ingredient(s), and optional ingredient(s), if necessary.

The method and means to mix the above essential and optional ingredients are not limited. Any conventional method and means can be used to mix the above essential and optional ingredients to prepare the formulation according to the present invention.

In a particular embodiment, the formulation of the invention is in a form imbuing a solid substrate, in particular a substrate formed from synthetic materials or formed from natural biodegradable and sustainably sourced natural originated fiber, natural fiber, or regenerated or recycled natural fiber, such as a wipe.

As used herein, the terms "comprising," "having," and "including" are used in their open, non-limiting sense. The terms "a," "an," and "the" are understood to encompass the plural as well as the singular. The expression "at least one" means one or more and thus includes individual components as well as mixtures/combinations.

All ranges and values disclosed herein are inclusive and combinable. For example, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The present disclosure will be further illustrated by the examples below.

BRIEF DESCRIPTION OF THE FIGURES

FIG. 4: Measurement of *S. aureus* turbidity reduction with time for *L. rhamnosus* GG lysate (concentrated 40×) and 20 mM acetate buffer pH 5 with or without lysostaphin (1 µg/mL). Time to reduce by half initial absorbance (IC50) is lower for lysostaphin in lysate compared to lysostaphin in acetate buffer. Lysate and acetate buffer in absence of lysostaphin have identical IC50. FIG. 5: Measurement of *S. aureus* CFU reduction with time for *L. rhamnosus* GG lysate (concentrated 40×) and 20 mM acetate buffer pH 5 with or without lysostaphin (1 µg/mL)

FIG. 11: Microscopy picture of scratch assay. Scratch assay on a Normal Human Epidermal Keratinocytes layer (NHEK) was performed and closure of the wound was monitored at T=0, 6, 12, 24 hours. Treatment with *L. rhamnosus* lysate allows a faster closure of the wound compared to treatment with IFN-γ or no treatment (control). FIG. 12: Quantification of wound-healing. Percentages of wound surface area decrease faster in presence of lysolysate compared to control or IFN-γ.

EXAMPLES

In the present examples, the inventors developed engineered postbiotics suitable to tackle diseases due to the growth of *S. aureus*, and demonstrated:
- a *S. aureus* specific killing activity based on a lysate containing lysostaphin,
- a synergistic increase in lysostaphin killing activity in presence of bacterial lysate,
- an anti-inflammatory effect to dampen the inflammatory response,
- a wound healing activity to repair barrier function, and
- a beneficial effect on host commensal microbiota.

Figure 1:
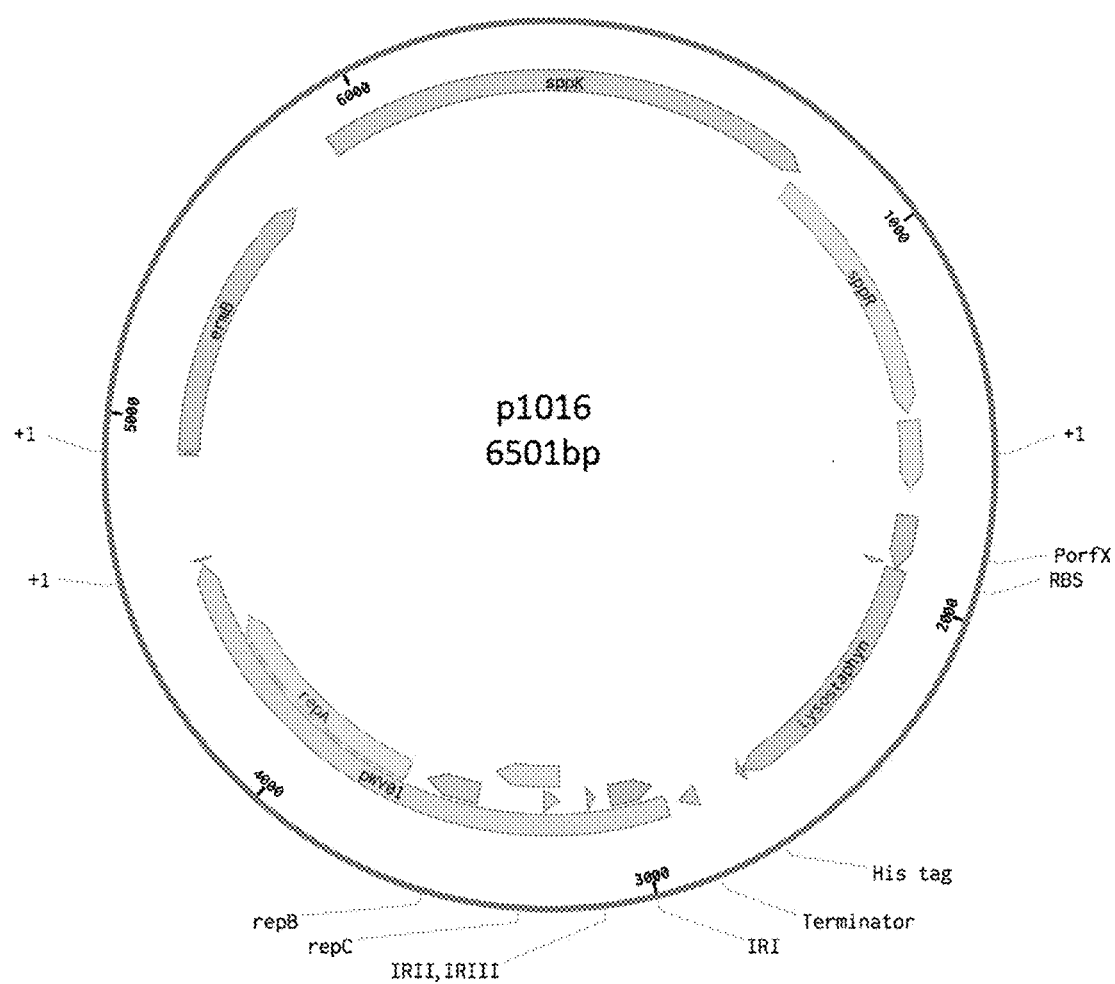
FIG. 1: Lysostaphin expression plasmid. p1016 plasmid map with His tagged Lysostaphin expressed from PorfX IP-673 inducible promoter. Plasmid backbone contains pWV01 origin of replication and an erythromycin resistance marker (ermB).

As a proof of principle, probiotic strain *L. rhamnosus* GG (LrOs11721) was engineered to express lysostaphin, a bacteriocin with high specificity for *S. aureus*. Lysostaphin was cloned on a plasmid (FIG. 1) under the control of the sakacin inducible promoter PorfX (Sørvig et al. (2005) Microbiology (Reading, England) 151:2439-2449) and transformed into *L. rhamnosus*. Transformants were grown, lysostaphin expression was induced at mid-log phase and cells were harvested at high density (OD~1). Bacterial cells were concentrated 40× in 25 mM sodium acetate buffer pH 5 by centrifugation before being lysed mechanically and filtered sterilized leading to a lysate (herein called lysolysate) containing both *L. rhamnosus* cell components and lysostaphin.

Example 1: *S. aureus* Specific Killing Using a *L. rhamnosus* Lysolysate

Figure 2:
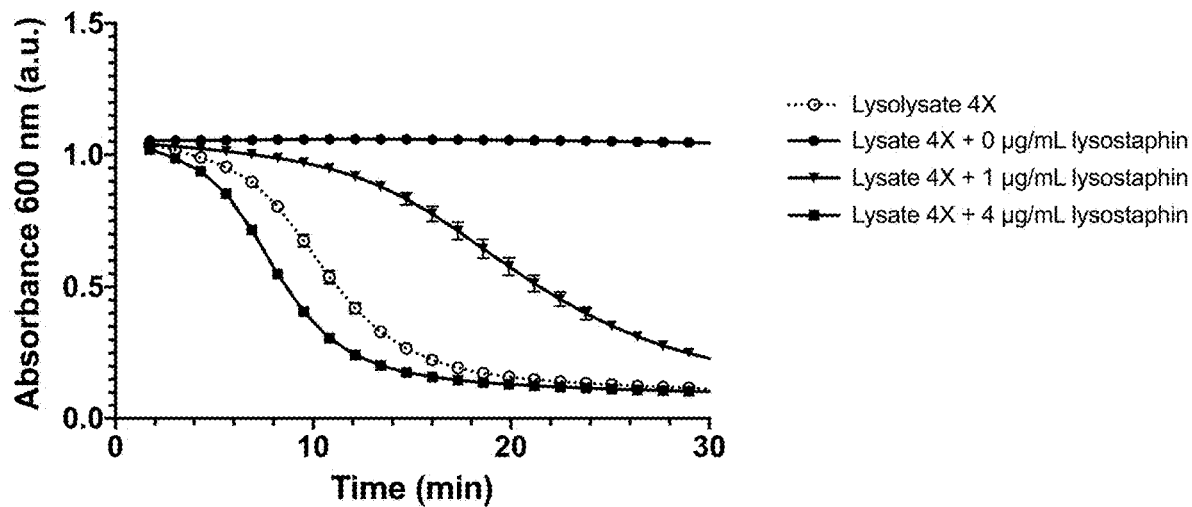
FIG. 2: Lysolysate killing activity. Measurement of *S. aureus* turbidity reduction with time when mixing *S. aureus* Newman strain with *L. rhamnosus* lysolysate produced from lysed culture of *L. rhamnosus* GG LrOs11721+p1016 expressing lysostaphin and concentrated 40× in 20 mM acetate buffer pH 5. *L. rhamnosus* GG LrOs11721 lysate was used as control and *L. rhamnosus* GG LrOs11721 lysates spiked with lysostaphin (1 and 4 µg/mL final concentration) as references.

In order to check the staphylolytic activity of the lysolysate, a turbidity reduction experiment was performed using *S. aureus* Newman strain mixed with lysolysate (FIG. 2). As shown in FIG. 2, a rapid decrease of the *S. aureus* population, as measured by absorbance at 600 nm, can be observed in the presence of the lysolysate. No decrease in absorbance was observed when *S. aureus* cells were put in the presence of *L. rhamnosus* lysate, indicating that the expressed Lysostaphin is responsible for the turbidity reduction and so the staphylolytic activity. Inventors decided to test the lysolysate killing specificity towards *S. aureus*.

Figure 3:
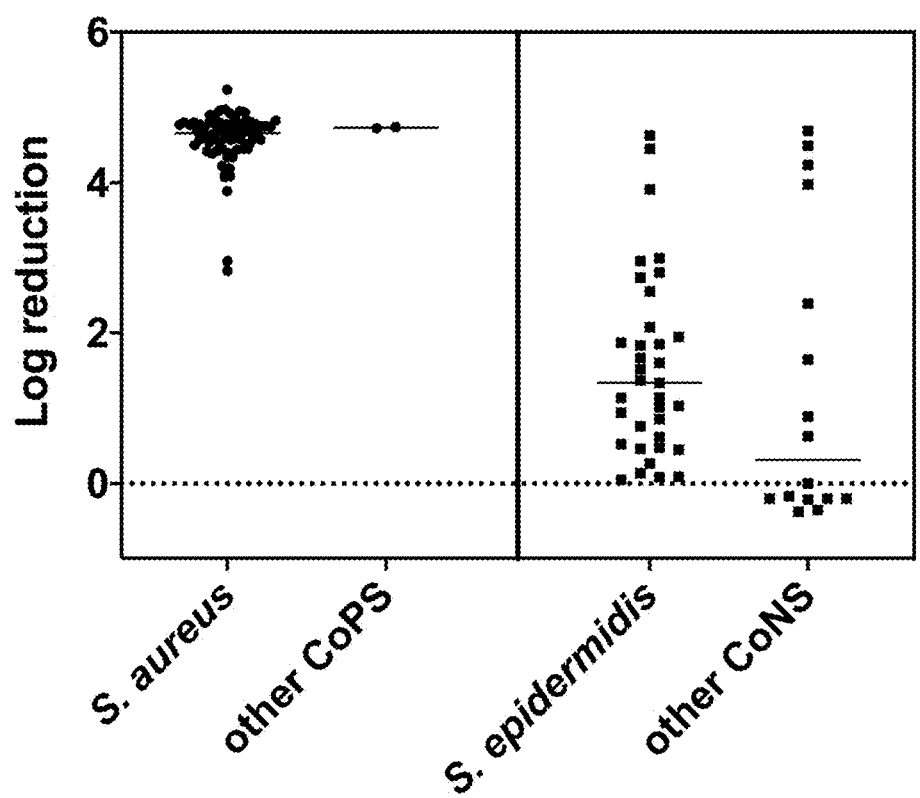
FIG. 3: Lysolysate specific and efficient killing of *S. aureus*. Log reduction (−log 10 (Final CFU/Initial CFU)) in *S. aureus* and other staphylococcal strains after 1 hour incubation with lysolysate.

Specificity of endolysin is generally at the genus level meaning that for example staphylococcal endolysins are able to kill both non-commensal species such as *S. aureus* but also commensal species such as *S. epidermidis*. Unlike endolysins, Lysostaphin has been shown to be specifically targeting *S. aureus* and show a much lower activity against other Staphylococcal species such as *S. epidermidis*. To test if the Lysostaphin-containing *L. rhamnosus* lysate has also a high *S. aureus* specificity, a killing assay was performed (FIG. 3) using lysolysate in presence of both Coagulase positive strains (CoPS) including 75 *S. aureus* strains and Coagulase negative strains (CoNS) including 35 *S. epidermidis* strains. An average of 4.58 log reduction was obtained for *S. aureus* strains against a 1.54 log reduction obtained against the 35 *S. epidermidis* strains. Thus lysolysate shows a high specificity towards *S. aureus* species.

Figure 4:
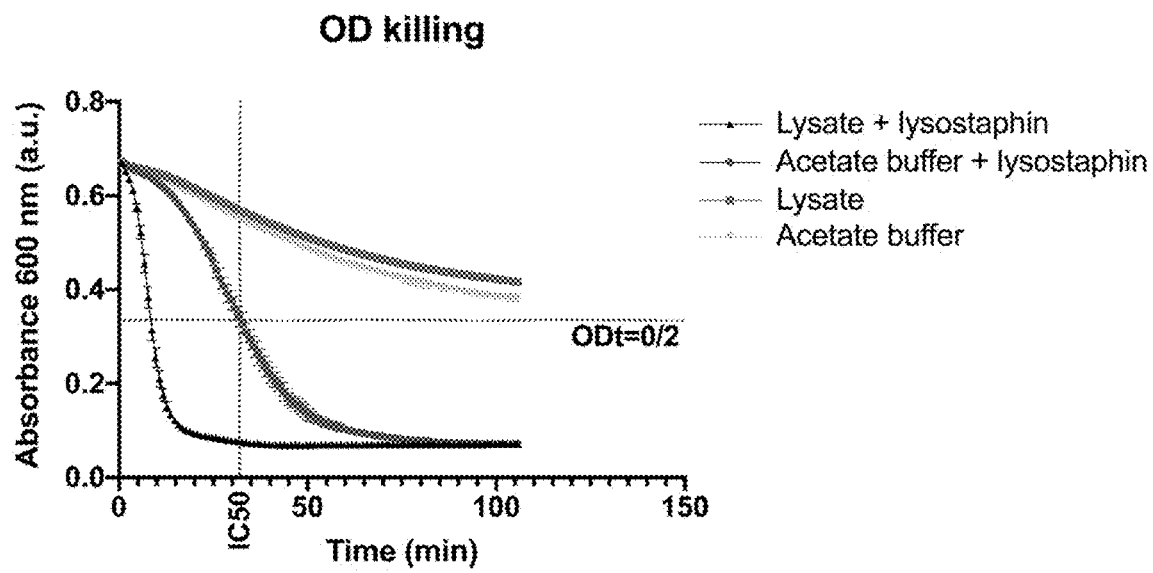
FIGS. 4 and 5: Synergistic effect of lysostaphin and bacterial lysates.
Figure 5:
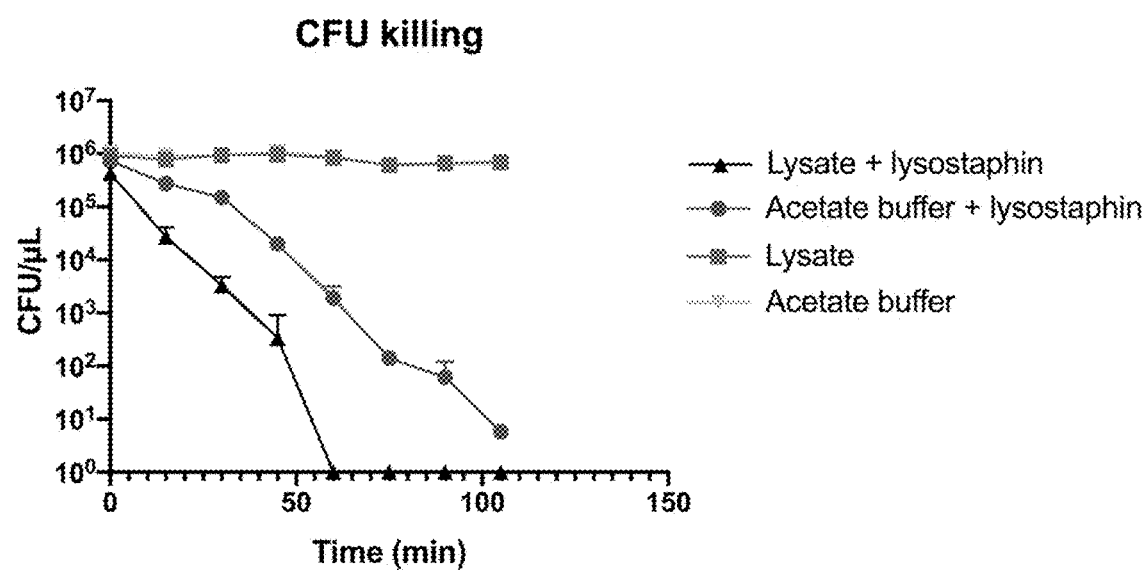

To quantify the effect of the bacterial lysate on Lysostaphin activity, a turbidity reduction experiment and a CFU experiment were performed (FIG. 4-5). The IC50, time to decrease initial OD by half, was measured for (i) *L. rhamnosus* lysate alone, (ii) 20 μg/ml of purified Lysostaphin (Sigma reference L9043) resuspended in 20 mM acetate buffer pH 5 (NaOAc) buffer and (iii) 20 μg/ml of purified Lysostaphin resuspended in *L. rhamnosus* lysate. Surprisingly, the inventors observed a higher turbidity reduction (lower IC50) and a faster decrease in CFU for the Lysostaphin in lysate compared to Lysostaphin in acetate buffer. No difference in turbidity reduction or CFU counts were measured between *L. rhamnosus* lysate and acetate buffer indicating that there is no activity of the *L. rhamnosus* lysate alone and the improvement of Lysostaphin activity in lysate is not the result of an additive effect of Lysostaphin activity and *L. rhamnosus* lysate activity but rather a synergistic effect of the lysate on the Lysostaphin activity. Such synergistic effect of Lysostaphin and bacterial lysate has not been documented and offers an advantageous and non-obvious effect for the killing of *S. aureus* with lysolysate compare to Lysostaphin alone.

Figure 6:
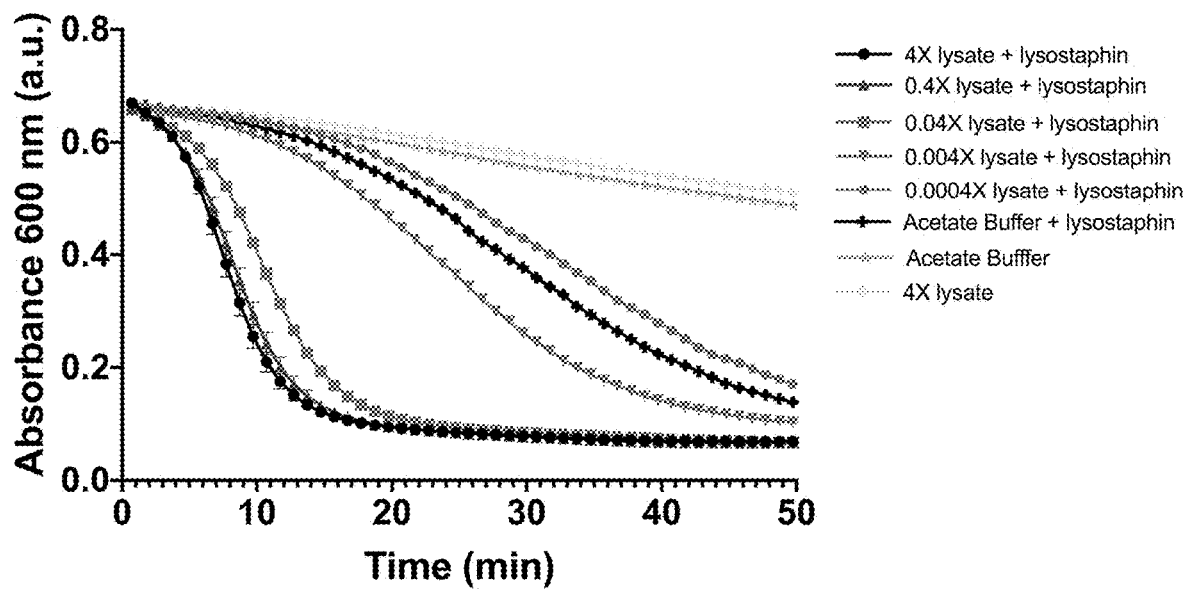
FIG. 6: Effect of lysate concentration on synergy. Measurement of *S. aureus* turbidity reduction with time for different concentrations of *L. rhamnosus* GG lysate (4×, 0.4×, 0.04×, 0.004×, 0.0004×) supplemented with Lysostaphin (1 µg/mL final concentration). Below a given concentration of lysate (between 0.004× and 0.0004×) the Lysostaphin killing activity is equivalent or lower than the same Lysostaphin concentration in acetate buffer.
Figure 7:
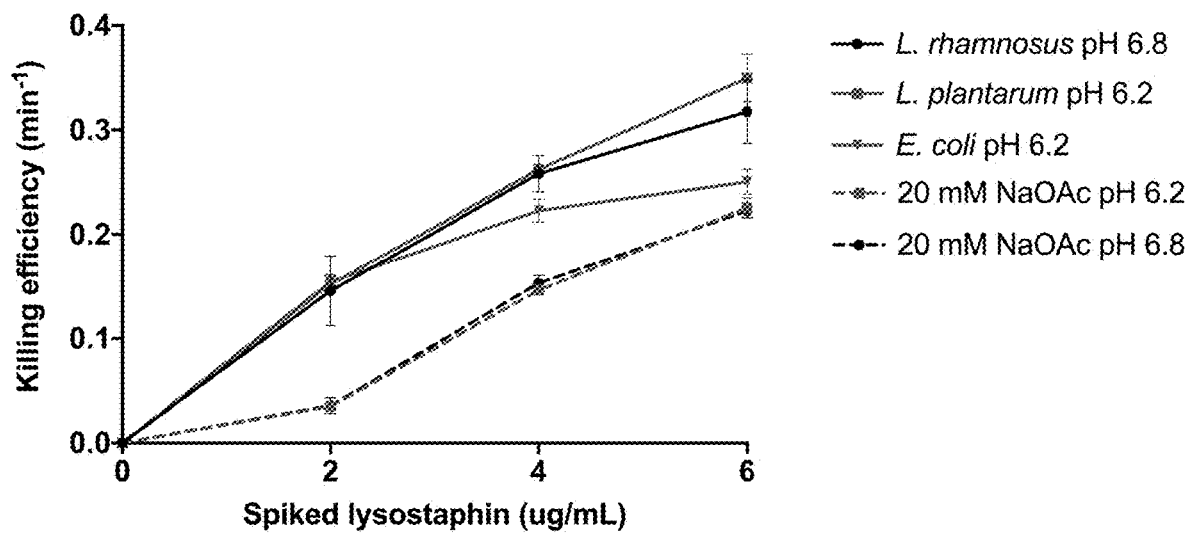
FIG. 7: Synergy effect on different bacterial strains. Measurements of *S. aureus* killing efficiency (1/IC50) for different bacterial lysates spiked with different concentrations of lysostaphin. A higher killing efficiency in bacterial lysate than in acetate buffer adjusted at equivalent pH is observed.

This synergistic effect between Lysostaphin and the *L. rhamnosus* lysate was observed for different concentrations of lysate (FIG. 6) and for different concentrations of Lysostaphin (FIG. 7).

To test if this effect was specific of *L. rhamnosus* lysate, *S. aureus* killing activity of Lysostaphin mixed with lysates from different bacteria (*Lactobacillus plantarum* and *Escherichia coli*) was measured. A synergistic effect was observed for both *Lactobacillus plantarum* and *E. coli* even if at higher Lysostaphin concentration (6 μg/ml) *E. coli* lysate killing activity was similar to the activity in buffer (FIG. 7).

The inventors also tested if the pH of the lysate could explain this synergy as it is known that acidic pH is not optimum for Lysostaphin activity. Lysate from *L. rhamnosus*, *L. plantarum* and *E. coli* were respectively pH 6.8, 6.2 and 6.2. *S. aureus* bactericidal activity was measured for different concentrations of Lysostaphin in acetate buffer with equivalent pH (6.2 and 6.8). A higher killing was still observed for the lysate compared to buffer at same pH (FIG. 7) indicating that the pH cannot explain the synergy observed.

Figure 8:
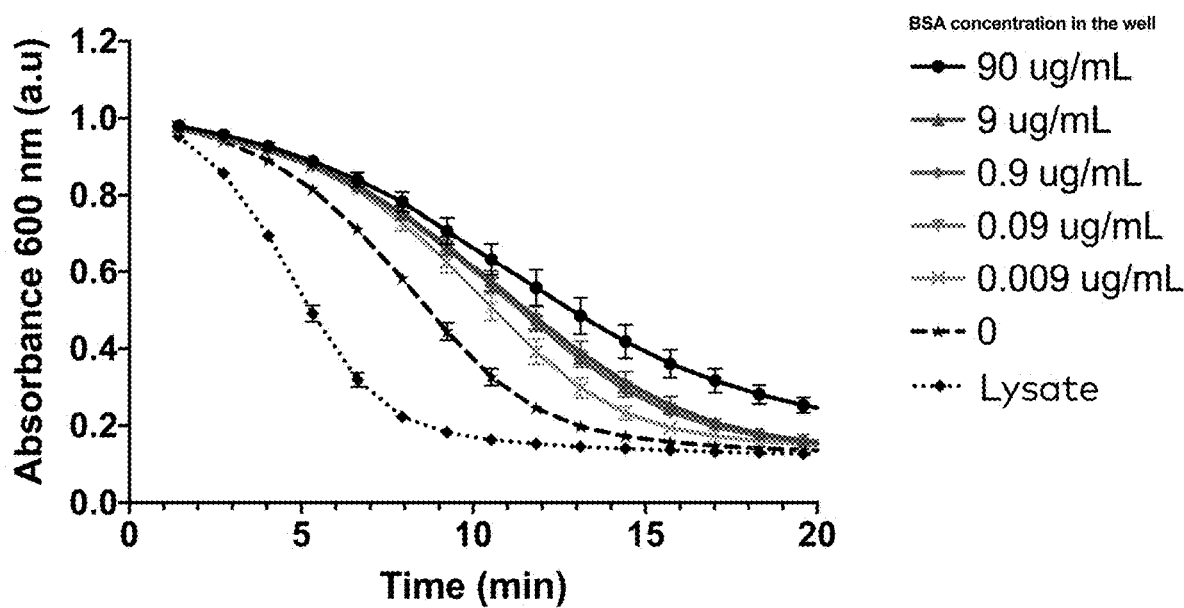
FIG. 8: Effect of molecular crowding on lysostaphin activity in acetate buffer. Measurements of *S. aureus* turbidity reduction in acetate buffer pH 5 with lysostaphin 4 µg/mL, supplemented with different concentrations of Bovine Serum Albumin (BSA) to increase molecular crowding, show a reduction in lysostaphin activity with higher molecular crowding.

One difference between Lysostaphin in acetate buffer and Lysostaphin in lysate is the presence of a large amount of proteins and other cellular molecules that might provide a high molecular crowding environment for Lysostaphin to act. In order to test if molecular crowding could explain the increased activity of Lysostaphin in bacterial lysate the inventors performed a turbidity reduction experiment in presence of increasing concentrations of Bovine Serum Albumin (BSA) (FIG. 8). All concentrations of BSA led to a slower decrease in turbidity indicating a lower Lysostaphin activity. Thus molecular crowding does not seem to explain the synergy effect observed between lysate and Lysostaphin.

The inventors have shown that a lysolysate, produced from the lysis of *L. rhamnosus* bacterial cells heterologously expressing cytoplasmic Lysostaphin, allows highly efficient and specific killing of *S. aureus* strains. Surprisingly inventors demonstrated a synergistic effect between Lysostaphin and *L. rhamnosus* lysate increasing Lysotaphin killing activity. This synergistic effect is not specific to *L. rhamnosus* lysate, and depends on the lysate concentration.

Materials and Methods:

Bacterial Strains:

*L. plantarum* s15998 was isolated from fermented cabbage. Lysolysate was produced from strain s18195 (*L. rhamnosus*+p1016).

Production of Bacterial Lysates:

Overnight cultures of *L. plantarum* s15998 was inoculated from cryostock in 50 mL of MRS (NutriSelect Merck) and incubated in anaerobic conditions at 37° C. Overnight culture of *L. rhamnosus* was inoculated from cryostock in 50 mL of SPY2 (Heenan, C. N., et al. (2002). Lwt-Food Sci Technology 35, 171-176) and incubated in anaerobic conditions at 37° C. Overnight culture of *E. coli* K-12 MG1655 liquid culture was grown in 50 mL LB (Difco) and incubated overnight in aerobic conditions at 37° C.

Overnight cultures were diluted 1/10 in 500 mL of the appropriate media pre-reduced in anaerobic conditions and incubated at 37° C. in anaerobic conditions except for *E. coli* that was incubated at 37° C. in aerobic conditions. At $OD_{600\ nm} \approx [1\text{-}2]$, bacterial cultures were put on ice, and the following steps were performed at 4° C. First cells were washed twice in deionized water using centrifugation and finally resuspended in 12.5 mL of 20 mM acetate buffer pH 5 (40× concentration of the initial cell culture). The concentrated culture was then lysed using bead beating at 30 Hz for 2 cycles of 20 minutes. Bacterial lysate was centrifuged for 10 min at 10 000 g and supernatant was then filtered (0.4 μm) and stored at 4° C. CFU counting was performed before and after bead beating treatment to measure lysis efficiency.

Production of Lysolysate:

Overnight culture of *L. rhamnosus* p1016 was inoculated from cryostock in 50 mL of SPY2 medium (Heenan, C. N., et al, (2002). Lwt-Food Sci Technology 35, 171-176) with erythromycin at a final concentration of 5 μg/mL and incubated in anaerobic conditions at 37° C. Overnight culture was diluted 1/10 in 500 mL of SPY2 medium pre-reduced in anaerobic conditions and incubated at 37° C. in anaerobic conditions. At an $OD_{600\ nm}$ of 0.3 the culture was induced with 200 ng/mL of inducing peptide IP-673 (Novopro Cat. #: 300935) and incubated at 37° C. until $OD_{600\ nm}=1.0$. Bacterial culture was put on ice, and the following steps were performed at 4° C. First cells were washed twice in deionized water using centrifugation and finally resuspended in 12.5 mL of 20 mM acetate buffer pH 5 (40× concentration of the initial cell culture). The concentrated culture was then lysed using bead beating at 30 Hz for 2 cycles of 20 minutes, placing the sample on ice for 2 minutes in between cycles. Bacterial lysate was centrifuged for 10 min at 10 000 g and supernatant was then filtered (0.4 μm) and stored at 4° C. CFU quantification was performed before and after bead beating treatment to measure lysis efficiency.

Turbidity Reduction Experiment:

Overnight culture of S. aureus strain Newman was inoculated from an isolated colony in 15 mL of TSB (Tryptic Soy Broth, Difco) and incubated at 37° C., aerobically. Overnight culture was diluted 1/100 in a final volume of 1.5 L of TSB and incubated aerobically at 37° C. At OD600 nm=1 culture was washed twice with deionised water at 4° C., centrifuged at 4° C., at 4000 g for 10 minutes, resuspended in 7.5 mL of 1×PBS (Phosphate Buffered Saline, Fisher BioReagents, pH 7.4) and finally frozen as 500 μL aliquots at −20° C.

Bacterial suspension for the turbidity reduction assay was prepared from an aliquot of the frozen stock of S. aureus strain Newman. Lysostaphin solution and bacterial suspension were mixed in a ratio 1:10 in duplicates in a 96-well plate (Microlon 200, transparent, flat bottom) in a final volume of 200 μL and absorbance at 600 nm (Tecan Infinite 200 pro) was measured every 1.3 minutes, at 37° C. without agitation for 1 hour.

Example 2: Beneficial Effect of Lysate on Skin Microbiota

The approach of the inventors aims at killing specifically S. aureus, as shown in example 1, but also helping the skin commensal bacteria to restore homeostasis by helping them grow and occupy the niche left empty from S. aureus decolonization.

Figure 9:
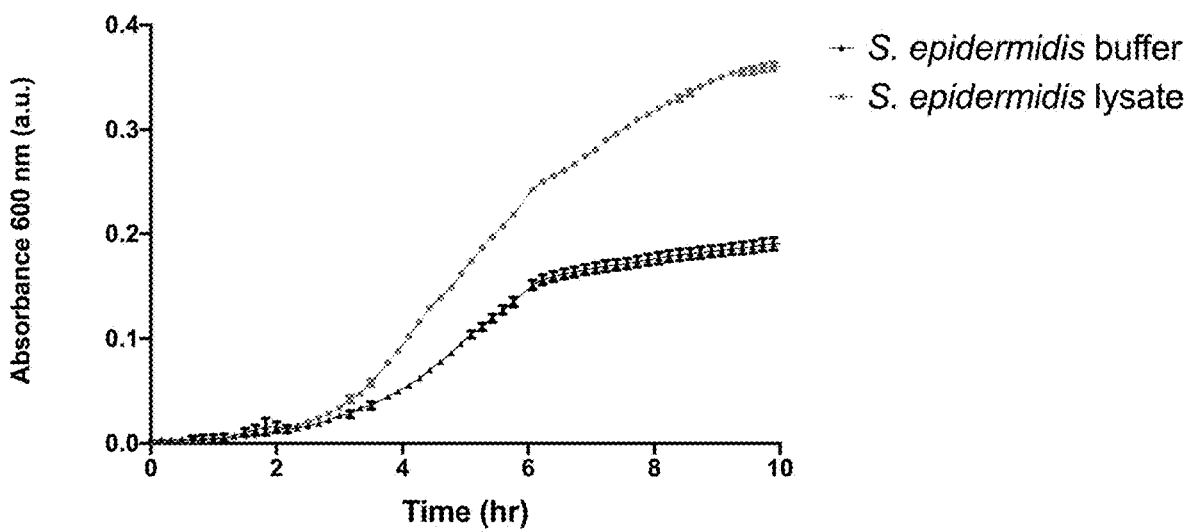
FIG. 9: Stimulation of *S. epidermidis* growth by *L. rhamnosus* lysate. Growth curve of *S. epidermidis* in diluted TSB (12.5% v/v) supplemented with 20 mM acetate buffer pH 5 or *L. rhamnosus* lysate.

To test such an effect, the inventors investigated the effect of the lysate on the growth of S. epidermidis (FIG. 9). S. epidermidis (ATCC® 12228™) was grown in poor nutrient conditions supplemented or not with L. rhamnosus lysate and cell density was followed by absorbance using $OD_{600\ nm}$ measurements. S. epidermidis shows a higher growth rate and final density in presence of L. rhamnosus lysate compared to buffer indicating a beneficial effect of the lysate on S. epidermidis.

Materials and Methods:

Production of L. ramnosus Lysate:

Overnight culture of L. rhamnosus was inoculated from cryostock in 50 mL of SPY2 (Heenan, C. N., et al. (2002). Lwt-Food Sci Technology 35, 171-176) and incubated in anaerobic conditions at 37° C. Overnight culture was diluted 1/10 in 500 mL of the appropriate media pre-reduced in anaerobic conditions and incubated at 37° C. in anaerobic conditions. At OD600 nm≈1, bacterial culture was put on ice, and the following steps were performed at 4° C. First cells were washed twice in deionized water using centrifugation and finally resuspended in 12.5 mL of 20 mM acetate buffer pH 5 (40× concentration of the initial cell culture). The concentrated culture was then lysed using bead beating at 30 Hz for 2 cycles of 20 minutes. Bacterial lysate was centrifuged for 10 min at 10 000 g and supernatant was then filtered (0.4 μm) and stored at 4° C. CFU was performed before and after bead beating treatment to measure lysis efficiency.

Growth Curve Experiment:

A preculture of S. epidermidis (ATCC® 12228™) was inoculated from cryostock into 10 mL TSB and incubated at 37° C. overnight. Overnight culture was washed twice in 12.5% (v/v) TSB, normalized to $OD_{600\ nm}=1$ and diluted 1/100 in 12.5% (v/v) TSB. In a 96 well plate, 180 μL of normalized bacterial culture was supplemented with 20 μL of L. rhamnosus lysate or 20 μL of 20 mM acetate buffer pH 5. Absorbance at 600 nm (Tecan Infinite 200 pro) was measured every 10 minutes, at 37° C. with agitation for a total of 10 hours.

Example 3: Anti-Inflammatory Effect

Another aspect of the engineered postbiotic of the present invention is its anti-inflammatory property. L. rhamnosus has already been shown to have anti-inflammatory properties, as a live probiotic (Sultana et al. (2013) Applied and Environmental Microbiology 79:4887-4894; Garcia et al. (2015) Applied and Environmental Microbiology 81:2050-2062), as a lysate or as killed probiotic (Mohammedsaeed et al. (2015) Scientific Reports 5:16147; Li et al. (2009) Pediatr Res 66:203-207). In order to test the anti-inflammatory properties of the lysate, the inventors used a LPS inflammation model on macrophage RAW-BLUE cells.

Briefly, growth culture of RAW-BLUE cells was supplemented with LPS or PBS and the cells were then treated with L. rhamnosus lysate or the buffer the lysate was prepared in.

Figure 10:
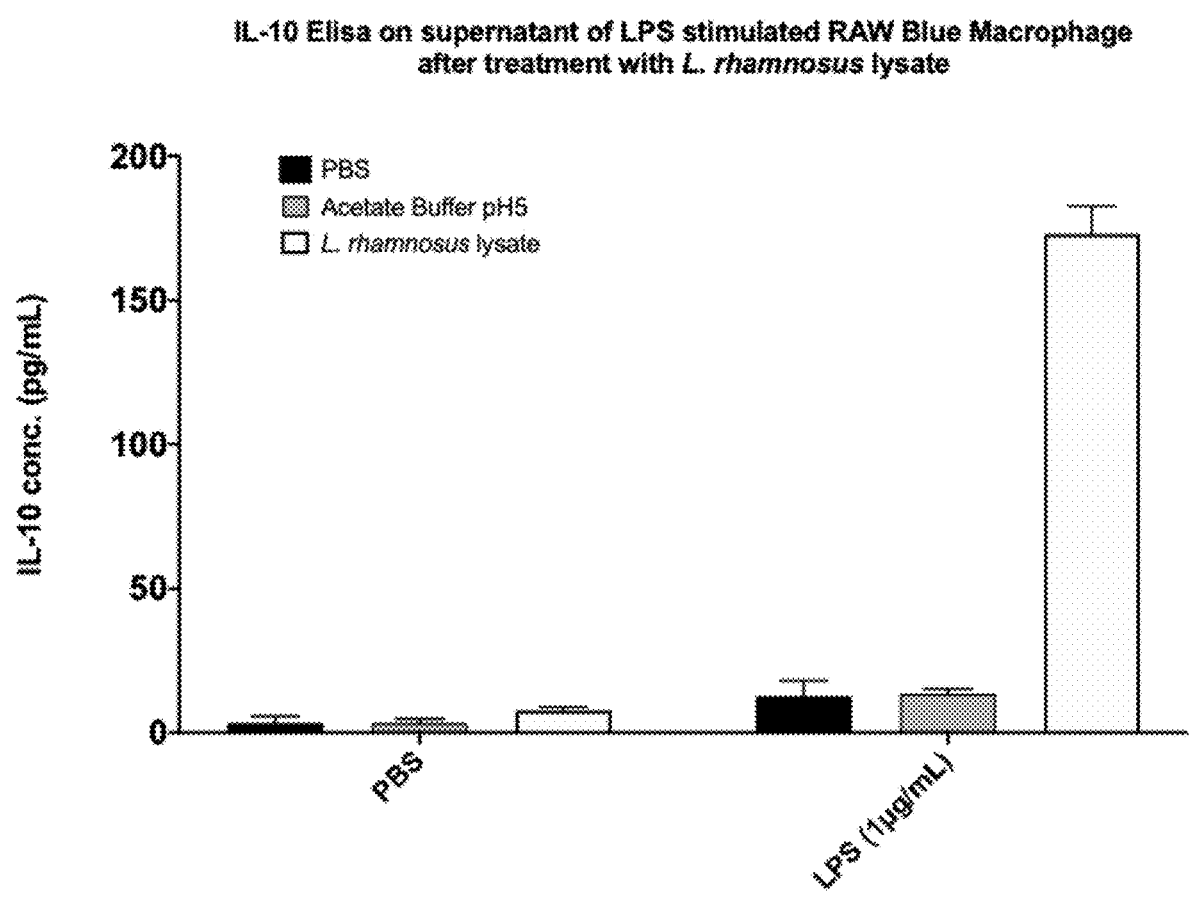
FIG. 10: Anti-inflammatory effect of *L. rhamnosus* lysate. IL-10 ELISA on supernatant of LPS stimulated RAW blue Macrophages after treatment with *L. rhamnosus* GG lysate. IL-10 concentration in supernatants of RAW-BLUE cells stimulated with LPS and treated with *L. rhamnosus* lysate is higher than when treated with 20 mM acetate buffer pH 5.

Seventeen hours after treatment the anti-inflammatory cytokine IL-10 was measured by ELISA in RAW-BLUE cells supernatant (FIG. 10). IL-10 levels were higher in the inflammation model after treatment with lysate compared to LPS treatment alone indicating a potential anti-inflammatory effect of the L. rhamnosus lysate.

Materials and Methods:

Production of L. Rhamnosus Lysate:

Overnight culture of L. rhamnosus was inoculated from cryostock in 50 mL of SPY2 (Heenan, C. N., et al. (2002). Lwt-Food Sci Technology 35, 171-176) and incubated in anaerobic conditions at 37° C. Overnight culture was diluted 1/10 in 500 mL of the appropriate media pre-reduced in anaerobic conditions and incubated at 37° C. in anaerobic conditions. At OD600 nm≈1, bacterial culture was put on ice, and the following steps were performed at 4° C. First cells were washed twice in deionized water using centrifugation and finally resuspended in 12.5 mL of 20 mM acetate buffer pH 5 (40× concentration of the initial cell culture). The concentrated culture was then lysed using bead beating at 30 Hz for 2 cycles of 20 minutes. Bacterial lysate was centrifuged for 10 min at 10 000 g and supernatant was then filtered (0.4 μm) and stored at 4° C. CFU enumeration was performed before and after bead beating treatment to measure lysis efficiency.

RAW-BLUE Cells Experiment:

RAW-BLUE cells macrophage were grown in DMEM-P/S-FBS cell culture media (DMEM, 4.5 g/l glucose, 10% heat-inactivated FBS, 100 U/mL of penicillin/streptomycin and 1 mM sodium pyruvate) with 200 μg/ml Zeocin and used once a confluency of 70-80% was reached. Cells were collected and diluted in DMEM-P/S-FBS (no zeocin) to 5.88e5 cells/mL and 170 μL was added to each well (~100, 000 cells/well). After 7 hours cells were stimulated with 10

μL of 20 μg/mL LPS (1 μg/mL final concentration in well) or 10 μL PBS as a control, followed by treatment with 20 μL of lysate or 20 mM acetate buffer pH 5. Approximately 17 hours after, supernatant was collected and used for ELISA.

IL-10 ELISA:

Using culture supernatant harvested from the Raw Blue cells inflammation model exp. An IL-10 elisa was performed as per manufacturer's instructions for the ELISA kit (Duo-Set® ELISA DEVELOPMENT SYSTEM ref: DY417-05). The standard curve was performed using the following concentrations of IL-10: 0, 7.8125, 15.625, 31.25, 62.5, 125, 250, 500 pg/mL.

Example 4: Wound Healing Activity to Repair Barrier Function

In addition to *S. aureus* bactericidal effects and stimulation of commensal bacteria, the inventors also explored the wound healing activity of the lysolysate. Indeed, *L. rhamnosus* lysate has been previously shown to promote wound healing (Mohammedsaeed et al. (2015) Scientific reports 5:16147) and stimulate barrier function (Sultana et al. (2013) Applied and Environmental Microbiology 79:4887-4894).

Figure 11:
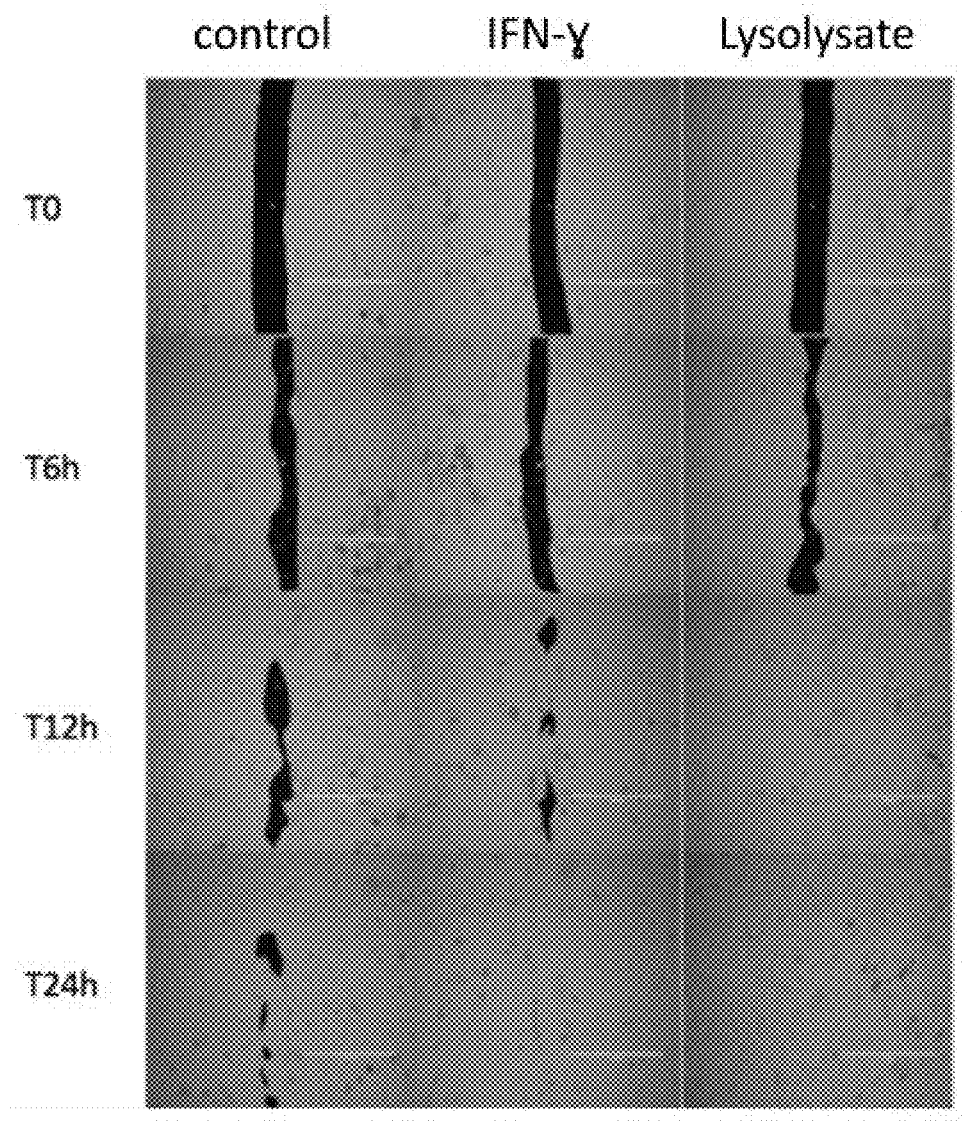
FIGS. 11 and 12: Wound Healing effect of *L. rhamnosus* lysate.
Figure 12:
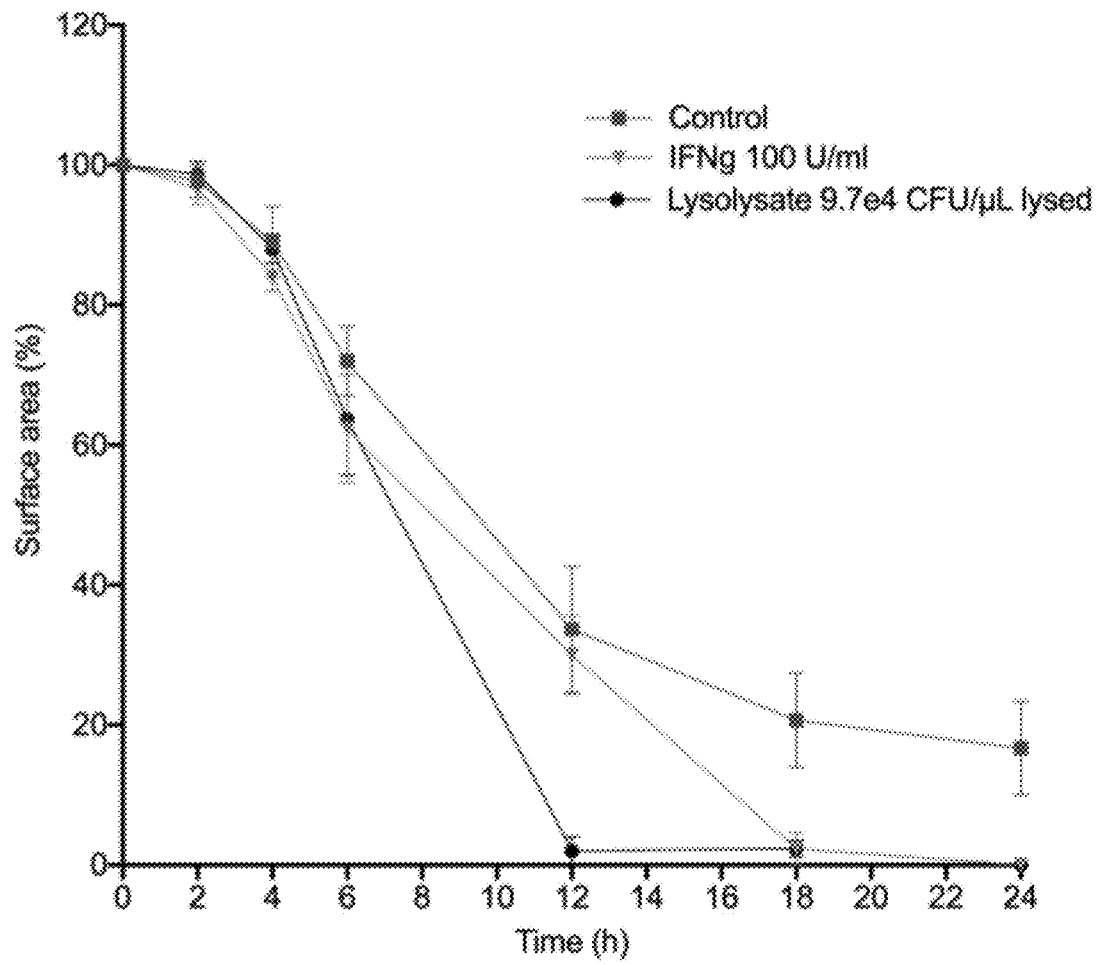

For that purpose, a scratch assay with keratinocytes in the presence of different concentrations of lysolysate was performed (FIGS. 11-12). A faster decrease in the surface of the wound was observed when lysolysate was added compared to control buffer or interferon gamma.

In conclusion the engineered postbiotics of the present invention show multiple activities that once combined on human skin should help resolve dysbiosis-induced disorders or diseases and reach homeostasis faster by:
  killing specifically the most frequent aetiological agent that is *S. aureus*, without negatively affecting the commensal skin population,
  stimulating growth of commensal skin population such as *S. epidermidis*,
  reducing inflammation and thus allowing de-escalation of associated symptoms (redness, itching), and
  promoting wound-healing thereby promoting barrier function of the skin.

Some of these activities should act synergistically to treat dysbiosis-induced disorders or diseases. For example by reducing inflammation and the associated production of human antimicrobial peptide, the engineered postbiotics could decrease impact on local skin microbiota whose growth will also be stimulated by the engineered postbiotics. In return, preserving the diversity of skin microbiota will help prevent dysbiosis resurgence and reappearance of diseases or disorders associated with such dysbiosis.

---

SEQUENCE LISTING

```
Sequence total quantity: 1
SEQ ID NO: 1            moltype = AA  length = 247
FEATURE                 Location/Qualifiers
source                  1..247
                        mol_type = protein
                        organism = Staphylococcus simulans
SEQUENCE: 1
MAATHEHSAQ WLNNYKKGYG YGPYPLGING GMHYGVDFFM NIGTPVKAIS SGKIVEAGWS    60
NYGGGNQIGL IENDGVHRQW YMHLSKYNVK VGDYVKAGQI IGWSGSTGYS TAPHLHFQRM   120
VNSFSNSTAQ DPMPFLKSAG YGKAGGTVTP TPNTGWKTNK YGTLYKSESA SFTPNTDIIT   180
RTTGPFRSMP QSGVLKAGQT IHYDEVMKQD GHVWVGYTGN SGQRIYLPVR TWNKSTNTLG   240
VLWGTIK                                                             247
```

---

The invention claimed is:

1. A formulation comprising an engineered postbiotic composition comprising a lysate of a *Lactobacillus rhamnosus* that heterologously expresses lysostaphin.

2. The formulation according to claim 1 further comprising at least one pharmaceutically acceptable excipient and/or adjuvant selected from the group consisting of disintegrants, binders, bulking agents/fillers, lubricants, glidants, wetting agents, penetration/permeation enhancers, mucoadhesive agents, preservatives, anti-foaming agents, suspending agents, viscosity modifying agents, coloring agents, antioxidants, and combinations thereof.

3. The formulation according to claim 1 further comprising an additional therapeutically active agent.

4. The formulation according to claim 2 further comprising an additional therapeutically active agent.

5. The formulation according to claim 1, said formulation being in the form of aqueous, hydroalcoholic or oily solutions, of dispersions in the form of solutions or dispersions of the lotion or serum type, of emulsions in particular with liquid or semi-liquid consistency of the milk type, typically obtained by dispersion of a fatty phase in an aqueous phase (O/W) or conversely (W/O), or suspensions or emulsions of soft semi-solid or solid consistency of the cream type, of cream, of aqueous or anhydrous gel, of microemulsions, of nanoemulsions, of microcapsules, of microparticles, of ionic and/or nonionic type vesicular dispersions, of stick, of aerosol spray, of pump spray, or of foam.

6. The formulation according to claim 5, said formulation being in the form of an emulsion, of a microemulsion or of a nanoemulsion.

7. The formulation according to claim 1, wherein said bacteria heterologously expressing said lysostaphin are GRAS and/or probiotic bacteria.

8. The formulation according to claim 1, wherein said bacteria heterologously expressing said lysostaphin have been genetically modified to express said lysostaphin.

9. The formulation according to claim 1, wherein said bacteria heterologously expressing said lysostaphin do not comprise any antibiotic resistance marker.

10. The formulation according to claim 1, wherein said postbiotic composition further comprises at least two different bacteriocins and/or endolysins.

11. The formulation according to claim 10, wherein said at least two different bacteriocins and/or endolysins target the same bacterial species.

12. The formulation according to claim 10, wherein said at least two different bacteriocins and/or endolysins target different bacterial species.

13. The formulation according to claim 1, wherein said postbiotic composition is in the form of a pharmaceutical formulation for topical application.

* * * * *